(12) United States Patent
Taniguchi et al.

(10) Patent No.: US 8,802,367 B2
(45) Date of Patent: Aug. 12, 2014

(54) METHODS FOR QUANTITATIVE CDNA ANALYSIS IN SINGLE-CELL

(75) Inventors: Kiyomi Taniguchi, Kokubunji (JP); Hideki Kambara, Hachioji (JP); Tomoharu Kajiyama, Higashiyamato (JP)

(73) Assignee: Hitachi, Ltd., Tokyo (JP)

( * ) Notice: Subject to any disclaimer, the term of this patent is extended or adjusted under 35 U.S.C. 154(b) by 400 days.

(21) Appl. No.: 11/783,575

(22) Filed: Apr. 10, 2007

(65) Prior Publication Data

US 2007/0281313 A1 Dec. 6, 2007

(30) Foreign Application Priority Data

May 30, 2006 (JP) ................................. 2006-150189

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| 5,759,820 A * | 6/1998 | Hornes et al. ................. 435/91.1 |
| 6,428,955 B1 * | 8/2002 | Koster et al. ...................... 435/6 |
| 2004/0086906 A1 | 5/2004 | Takiguchi |
| 2005/0153292 A1 * | 7/2005 | Stordeur et al. .................. 435/6 |
| 2006/0177836 A1 * | 8/2006 | McKernan et al. ............... 435/6 |

FOREIGN PATENT DOCUMENTS

| JP | 2005-046138 | 7/2004 |
| WO | WO 03/106680 A1 | 6/2003 |
| WO | WO 2004/104181 A2 | 5/2004 |

OTHER PUBLICATIONS

Invitrogen Application Note, "Automated mRNA Purification using the Dynabeads® mRNA DIRECT™ on Tecan Freedom EVO®," Invitrogen, printed Apr. 2006, pp. 1-4.*

Fellmann et al., "Removal Simplified Protocol of Solid-Phase cDNA Libraries for Multiple PCR Amplification," Biotechniques, 1996, vol. 21, No. 5, pp. 766, 768, and 770.*
Cote et al., "A Technique for the Generation of a Stable and Reusable Source of cDNA from Human Blood or Tissue," Biochemica, 1997, No. 4, pp. 14-18.*
Hartshorn C. et al., BMC Biotechnology, vol. 5, No. 2, pp. 1-13 (Jan. 2005).*
Klein, C. A. et al., Nature Biotechn., vol. 20, pp. 387-392 (2002).*
Invitrogen Dynabeads Oligo (dT)25, Rev. No. 006 (downloaded May 11, 2009).*
Lambert, K.N. et al., Nucl. Acids res., vol. 21, pp. 775-776 (1993).*
Fan, Z. H. et al., Anal. Chem., vol. 71, pp. 4851-4859 (1999).*
Jones, Mark A. and Grierson, Claire S., "A simple method for obtaining cell-specific cDNA from small numbers of growing root-hair cells in *Arabidopsis thaliana*," Society for Experimental Biology, Journal of Experimental Botany, vol. 54 No. 386, May 2003, pp. 1373-1378.
Klein, Christoph A., "Single cell amplification methods for the study of cancer and cellular ageing," Mechanisms of Ageing and Development, vol. 126 (2005), pp. 147-151.
European Office Action dated Oct. 9, 2008 regarding European Application No. 07 008 984.2-1222.
Kyomi Taniguchi et al., "Quantitative analysis of gene expression in a single cell by qPCR", Nature Methods, vol. 6, No. 7, Jul. 2009, pp. 503-506; Epub Jun. 14, 2009.

* cited by examiner

*Primary Examiner* — Teresa E Strzelecka
(74) *Attorney, Agent, or Firm* — Stephen J. Weyer, Esq.; Stites & Harbison, PLLC.

(57) ABSTRACT

It is an object to provide a method of suitably analyzing the amount of gene expression of a single-cell.
A method of detecting a nucleic acid comprising
a step of sampling a single-cell from a sample containing at least a single-cell,
a cell lysis step of lysing cell membrane of the sampled single-cell and extracting nucleic acids from the cell,
a DNase treatment step of degrading DNA of the extracted nucleic acids with DNase,
a step of hybridizing mRNA of the total RNA contained in the single-cell with oligo (dT) fixed onto a carrier,
a step of performing reverse transcription of the mRNA hybridized with the oligo (dT) to fix cDNA derived from the single-cell onto the carrier, thereby preparing a single-cell derived cDNA library fixed onto a carrier, and
a step of amplifying cDNA fixed onto the carrier and simultaneously detecting an amplification amount of the cDNA.

9 Claims, 12 Drawing Sheets

SEQUENCE LISTING

<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
tttttttttt tttttttttt tttttttttt                                    30

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
ccgtgtgaac catgtgactt                                               20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 3
caacctgctc agatacatca aac                                                23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
agctgcaatc tcatcactgg                                                    20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
tgatggcaag agatgttcac t                                                  21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 6
agcactggag gaagcacac                                                     19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
gaagcaaggg acaaaggtaa                                                    20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
gagctgtgat gtgaagtttc c                                                  21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 9
ggaggcaagg gtacatgag                                                     19

<210> SEQ ID NO 10
<211> LENGTH: 19
<212> TYPE: DNA
<213> ORGANISM: Artificial Sequence

```
<220> FEATURE:
<223> OTHER INFORMATION: Description of Artificial Sequence: primer

<400> SEQUENCE: 10
gcatcatgga ggtttgaag                                                    19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 11 tataaccecta cattttgtgc at                                               22

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 12
tttccgctga gtccagatt                                                    19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 13
ccctgattga aggctttg                                                     18

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 14
cactgggaag gtcactctg                                                    19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 15
ttctgtcatc accacatctt g                                                 21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 16
acccaccaac aatttagtag ttat                                              24
```

```
<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 17
gctctgactt tagcacctgt ta                                                  22

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: probe

<400> SEQUENCE: 18
cgcatttgga ttggatga                                                       18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: probe

<400> SEQUENCE: 19
tggactacga gtcatacaca                                                     20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: probe

<400> SEQUENCE: 20
ccattcgctc ctactgat                                                       18

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: probe

<400> SEQUENCE: 21
agccagagtt atttcctgg                                                      19
```

US 8,802,367 B2

METHODS FOR QUANTITATIVE CDNA ANALYSIS IN SINGLE-CELL

CLAIM OF PRIORITY

The present application claims priority from Japanese application JP 2006-150189 filed on May 30, 2006, the content of which is hereby by reference incorporated into this application.

BACKGROUND OF THE INVENTION

1. Field of the Invention

The present invention relates to methods for quantitative analysis for gene expression using as an analysis sample a library of single-cell derived cDNA fixed onto a carrier, which is formed by immobilizing cDNA derived from a single-cell onto a carrier. The present invention also relates to methods for quantitative analysis for gene expression using as an analysis sample a library of cDNA fixed onto a carrier, which is formed by immobilizing cDNA derived from a small number of cells onto a carrier.

2. Background Art

As conventional methods for gene expression analysis, typically mention is made of a microarray method and a real-time PCR method. In these conventional methods, a tissue slice consisting of a plurality of cells or a plurality of cultured cells (about $10^6$) is often used as an analysis sample. In actual cells, since the expression amount of a gene variously changes with time, the expression of the gene varies per cell with time depending upon the site even in the same tissue. Therefore, when tissues and a plurality of cells are analyzed as a sample, variances between cells in measurement value are usually averaged. From the data thus obtained, it is difficult to obtain detailed information of a living organism having dynamical changes. Now that individual cells, which are minimum units of life for carrying out a biological activity, have different life phenomena from each other, it is difficult to integrally analyze living activity in a single cell and between cells by conventional gene expression analysis using a plurality of cells as an analysis sample.

Recently, there has been a growing trend to see life as a system. A minimum unit of the system of life is a cell. To elucidate the system of life, it is necessary to analyze all molecules contained in a single-cell and elucidate the cell integrally. For example, in the tissues concerning with in-vivo information transmission involving hormones and neurotransmitters and the embryo tissue in a development stage, it is considered that the amount of gene expression greatly differs between cells. Therefore, gene expression analysis at a single-cell level is highly required.

Recently, with remarkable technical developments in reagents and detection devices, etc., analysis of gene expression at a single-cell level has become feasible and interesting findings in the molecular biology have been reported and received attention. However, the amount of mRNA contained in a single-cell is extremely low. A problem of detection sensitivity has not yet completely solved and a gene that can be analyzed is still limited to highly expressing ones.

At the era of genome analysis, technical development has been made with focusing on how efficiently an unknown DNA sequence is read. In contrast, at the post genome era, to interpret a cell as a system, it is required to develop a means for analyzing, with a high sensitivity, from which gene mRNA expressed in individual single-cells is derived, and how much amount the mRNA is present. Under the circumstances, to efficiently recover mRNA molecules and synthesize cDNA, a method of capturing mRNA by use of oligo (dT) fixed magnetic beads and subjecting the mRNA to reverse transcription has been proposed (JP Patent Publication (Kokai) Nos. 2002-238575 and 2005-46138).

The aforementioned conventional techniques may have the following technical problems. First, in the methods according to these patent documents, 1 μg of RNA (corresponding to the amount of RNA of $10^5$ cells) is extracted and purified from a plurality of cells in advance and diluted to prepare an RNA solution containing a small amount of RNA, which is used as a starting material. More specifically, RNA, in actual, is not extracted from a single-cell. The RNA extraction methods and purification methods set forth in the patent documents require operations of repeatedly transferring a sample from a tube to another tube, allowing a column to absorb RNA and repeatedly washing the column. Through these operations, a sample of RNA runs out. Therefore, it is difficult to recover an extremely small amount of RNA (about 10 pg) contained in a single-cell. Furthermore, in such conventional methods, recovering rates differ between individual samples. Thus, they are unfavorable for quantitative analysis. Furthermore, in each of the methods according to the patent documents, after reverse transcription is performed on the magnetic beads, a customary PCR amplification is performed. The absolute total number and ratio of RNA molecules derived from various types of genes which are present in an original sample are varied by the amplification step. Therefore, these mRNA cannot be used as a sample for quantitative analysis.

On the other hand, a reagent kit for a single-cell gene expression analysis is commercially available, by which a cell lysis step, DNase treatment step, and reverse transcription step are carried out in a single tube. Synthesis of cDNA by the reagent kit is easily performed and free from conventional problems such as a loss of an analysis sample during extraction and purification processes of a nucleic acid and variance in yield. However, a residual reagent remains in a cDNA solution synthesized by the reagent kit and inhibits a PCR amplification reaction. Therefore, it is difficult to perform a real-time PCR analysis using the whole amount of cDNA derived from a single-cell. To reduce the inhibition of PCR amplification by the residual reagent, cDNA derived from a single-cell is further divided into portions and a portion has to be used for analysis. As a result, detection sensitivity of the real-time PCR analysis greatly decreases. In addition, cDNA derived from a single-cell is consumed as analysis proceeds. The types of genes that can be analyzed are limited.

SUMMARY OF THE INVENTION

The present invention was made in view of the aforementioned problems. An object of the present invention is to provide a method of suitably and quantitively analyzing gene expression in a single-cell.

The present inventors have conducted intensive studies with a view to solving the aforementioned problem. As a result, they confirmed that cDNA can be synthesized on a carrier surface from an extremely small amount of mRNA present in a single-cell without losing mRNA by performing a step of lysing a single-cell in a single tube, a step of treating a cell lysate with DNase, and a step of performing reverse transcription using a carrier having oligo (dT) fixed thereon, in the single tube. Based on this, it was found that a single-cell derived cDNA library fixed onto a carrier, which is derived from an extremely small amount of mRNA derived from the single-cell, can be prepared, and that purification and recovery of a small amount of cDNA at a single-cell level, which is not virtually attained by conventional methods, can be easily attained.

Furthermore, they found that when the single-cell derived cDNA library fixed onto a carrier is directly used as an analysis sample and real-time PCR is performed, its quantification performance can be maintained. Moreover, they found that the library can be repeatedly used as an analysis sample for quantitative analysis by washing the library after analysis and solve the problems of conventional methods, such as inhibition of PCR with a residual reagent in a sample, a sensitivity decrease caused by use of a portion of an analysis sample, and a limited number of genes analyzed.

More specifically, the present invention encompasses the following inventions.

(1) A method of detecting a nucleic acid comprising
a step of sampling a single-cell from a sample containing at least a single-cell,
a cell lysis step of lysing cell membrane of the sampled single-cell and extracting nucleic acids from the cell,
a DNase treatment step of degrading DNA of the extracted nucleic acids with DNase,
a step of hybridizing mRNA of the total RNA contained in the single-cell with oligo (dT) fixed onto a carrier,
a step of performing a reverse transcription of the mRNA hybridized with the oligo (dT) to fix cDNA derived from the single-cell onto the carrier, thereby preparing a single-cell derived cDNA library fixed onto a carrier, and
a step of amplifying cDNA fixed onto the carrier and simultaneously detecting an amplification amount of the cDNA.

(2) The method of detecting a nucleic acid according to item (1) in which the cell lysis step, the DNase treatment step, the step of hybridizing mRNA of the total RNA contained in the single-cell with oligo (dT) fixed onto a carrier, and a step of performing a reverse transcription of the mRNA hybridized with oligo (dT) to fix cDNA derived from the single-cell onto the carrier, thereby preparing a single-cell derived cDNA library fixed onto a carrier, are performed in a single tube.

(3) The method of detecting a nucleic acid according to item (1), further comprising, after a step of amplifying cDNA fixed onto the carrier and simultaneously detecting an amplification amount of the cDNA, a step a of recovering and washing the carrier and step b of amplifying the cDNA fixed onto the carrier and simultaneously detecting the amplified amount.

(4) The method of detecting a nucleic acid according to item (3), further comprising, after the step b, a step of repeating the step a and the step b.

(5) The method of detecting a nucleic acid according to item (1), in which, in the step of preparing a single-cell derived cDNA library fixed onto a carrier, substantially all mRNA molecules contained in the single-cell are hybridized.

(6) The method of detecting a nucleic acid according to item (1), in which the carrier consists of particles and the total surface area of the particles is 0.1 cm$^2$ or more.

(7) The method of detecting a nucleic acid according to item (1), in which the carrier consists of particles and a volume occupancy rate of the particles in an amplification reaction solution is 1% or less.

(8) The method of detecting a nucleic acid according to item (1), in which the carrier consists of particles and a volume occupancy rate of the particles in an amplification reaction solution is 0.1% or less.

(9) The method of detecting a nucleic acid according to item (1), in which the total number of oligo (dT) molecules fixed onto the carrier is 10$^{12}$ or more.

(10) The method of detecting a nucleic acid according to any one of items (6) to (9) in which the diameter of the particles is 1 μm and the number of the particles is 10$^7$ to 10$^8$.

(11) The method of detecting a nucleic acid according to any one of items (6) to (9), in which the diameter of the particles is 2.8 μm and the number of the particles is 10$^6$ to 10$^7$.

(12) The method of detecting a nucleic acid according to any one of items (6) to (11), in which the particles are magnetic beads.

(13) A method of detecting a nucleic acid comprising
a step of sampling a plurality of cells as large as 10$^3$ or less from a sample containing cells,
a cell lysis step of lysing cell membrane of the sampled cells and extracting nucleic acids from the cells,
a DNase treatment step of degrading DNA of the extracted nucleic acids with DNase,
a step of hybridizing mRNA of the total RNA contained in the cells with oligo (dT) fixed onto a carrier,
a step of performing a reverse transcription of the mRNA hybridized with oligo (dT) to fix cDNA derived from the cells onto the carrier, thereby preparing a cDNA library fixed onto a carrier, and
a step of amplifying cDNA fixed onto the carrier and simultaneously detecting an amplification amount of the cDNA.

According to the present invention, purification and recovery of a small amount of cDNA at a single-cell level, which has been difficult to perform by conventional methods, can be easily performed by preparing a single-cell derived cDNA library fixed onto a carrier. Furthermore, since a residual reagent (such as cell lysis reagent and DNase reagent) remaining in a sample in conventional methods can be removed, PCR inhibition with the residual reagent cannot be taken into consideration, and therefore, a whole amount of cDNA sample derived from a single-cell can be subjected to an amplification reaction without dividing the cDNA sample into portions. More specifically, PCR analysis can be performed with a higher sensitivity than those of the conventional methods.

BRIEF DESCRIPTION OF THE DRAWINGS

FIG. 9-1 is a graph of magnetic beads of 1 μm in diameter and FIG. 9-2 is a graph of magnetic beads of 2.8 μm in diameter. The transverse axis indicates the number of magnetic beads used in reverse transcription and the vertical axis indicates the number of copies/single-cell;

FIG. 10-1 shows the results with respect to an optimal total surface area of a carrier in a step of performing reverse transcription of mRNA derived from a single-cell on the surface of a carrier in the method of the present invention. The transverse axis indicates the total surface area (cm$^2$) of carrier and the vertical axis indicates the number of copies/single-cell;

FIG. 10-2 shows the same graph as in FIG. 10-1 except that the total number of oligo (dT) molecules fixed on the surface of a carrier is plotted on the transverse axis;

FIG. 11-1 is a graph of magnetic beads of 1 μm in diameter and FIG. 11-2 is a graph of magnetic beads of 2.8 μm in diameter. The transverse axis indicates the number of template molecules and the vertical axis indicates a Ct (threshold cycle) value.

DETAILED DESCRIPTION OF THE PREFERRED EMBODIMENTS

Figure 1:
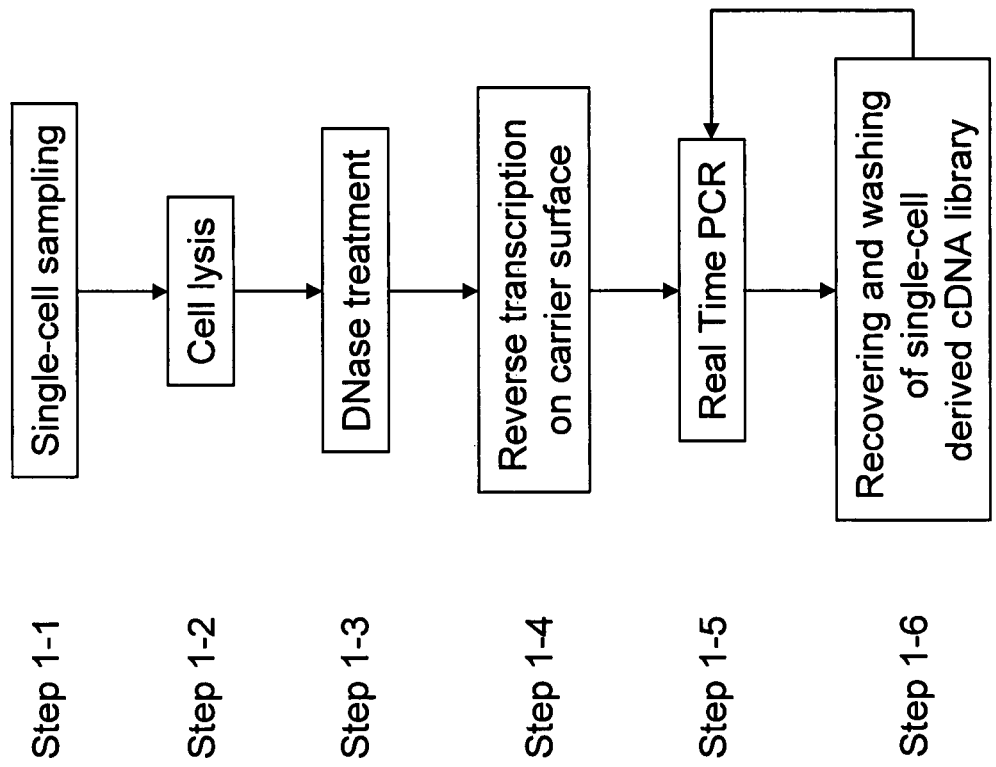
FIG. 1 shows a flowchart of an embodiment of the nucleic acid detection method of the present invention.

The present invention is directed to a method of detecting a nucleic acid comprising, a step of sampling a single-cell from a sample containing at least a single-cell, a cell lysis step of lysing cell membrane of the sampled single-cell and extracting nucleic acids from the cell, a DNase treatment step of degrading DNA of the extracted nucleic acids with DNase, a step of hybridizing mRNA of the total RNA contained in the single-cell with oligo (dT) fixed onto a carrier, a step of performing a reverse transcription of the mRNA hybridized with the oligo (dT) to fix cDNA derived from the single-cell onto the carrier, thereby preparing a single-cell derived cDNA library fixed onto a carrier, and a step of amplifying cDNA fixed onto the carrier and simultaneously detecting an amplification amount of the cDNA. In order to avoid a sample loss, the operations from the cell lysis step to a step of immobilizing cDNA derived from the single-cell onto the carrier, thereby preparing a single-cell derived cDNA library fixed onto a carrier, are preferably performed in a single tube.

The sample containing at least a single-cell is not particularly limited as long as it contains mRNA such as animal, vegetable and microbial cells and tissues. The step of sampling a single-cell from a sample can be performed by a customary method in the art. For example, cultured cells are treated with trypsin, thereby removing and suspending cells. After trypsin is inactivated, the resultant cell suspension is centrifuged and the supernatant is removed. The obtained cell mass is suspended in a buffer. The suspension buffer is diluted up to a cell concentration of about 500 cells/mL while counting the number of cells by a hemocytometer. A single-cell is suctioned from a liquid drop of the diluted cell solution by a pipette under microscopic observation and discharged in a tube. To avoid degradation of RNA, the cell thus sampled is preferably stored at low temperature.

The cell lysis step of lysing cell membrane of the single-cell and extracting nucleic acids from the cell can be performed by use of a proteolytic enzyme such as Proteinase K, a chaotropic salt, e.g., guanidine thiocyanate or guanidine hydrochloride, or a surfactant such as Tween or SDS. In this step, nucleic acids, namely DNA and RNA, contained in the single-cell sampled in the previous step can be extracted from the cell.

Subsequently, of the nucleic acids extracted in the cell lysis step, DNA is degraded by DNase. In this manner, genomic DNA contained in the cell lysate can be degraded to obtain a sample containing only RNA as a nucleic acid. More specifically, a cell lysate, after DNase I or the like is added thereto, is incubated. Immediately after the reaction, EDTA is added and DNase I is inactivated by heating.

In the following step, mRNA of the total RNA contained in the single-cell is hybridized with oligo (dT) fixed onto a carrier. Preferably, substantially all mRNA molecules contained in the single-cell are hybridized. Since mRNA contains a poly A sequence, hybridization is performed by use of oligo (dT) having a complementary sequence to the poly A sequence to bind mRNA alone of the total RNA contained in the single-cell to the carrier. Oligo (dT) can be synthesized by a customary method. The polymerization degree of the oligo (dT) may be sufficient if the poly A sequence of mRNA can be hybridized with it to bind mRNA to the carrier onto which the oligo (dT) is fixed thereon. If the polymerization degree of oligo (dT) is set at a predetermined value or more, hybridization with the poly A sequence can be maintained, thereby preventing a decrease of mRNA capturing rate. On the other hand, if the polymerization degree of oligo (dT) is set at a predetermined value or less, a decease in a rate of immobilizing oligo (dT) on the surface of a carrier can be prevented, and formation of a higher-order structure can be prevented, thereby preventing inhibition of hybridization with the poly A sequence of mRNA. Accordingly, the polymerization degree of oligo (dT) is generally 5 to 200 and preferably 20 to 40. Furthermore, in place of oligo (dT), another sequence containing a complementary sequence to the poly A sequence of mRNA, such as poly U, can be used. This case is also encompassed in the present invention.

The carrier on which oligo (dT) is to be fixed may not be particularly limited as long as it is insoluble in water and not melted during a denaturing step with heat. Examples of the carrier include metals such as gold, silver, copper, aluminium, tungsten, molybdenum, chromium, platinum, titanium and nickel; alloys such as stainless steel, hastelloy, Inconel, Monel metal, and duralumin; silicon; glass materials such as glass, quartz glass, fused quartz, synthetic quartz, alumina, sapphire, ceramic, forsterite and photosensitive glass; plastics such as polyester resin, polystyrene, polyethylene resin, polypropylene resin, ABS resin (acrylonitrile butadiene styrene resin), nylon, acrylic resin, fluoride resin, polycarbonate resin, polyurethane resin, methylpentene resin, phenolic resin, melamine resin, epoxy resin and vinyl chloride resin; agarose; dextran; cellulose; polyvinyl alcohol; nitrocellulose; chitin; and chitosan. The shape of the carrier is not particularly limited and may include a titer plate, flat plate, film, tube and particles. When particles are employed as a carrier, a large surface area per unit volume can be advantageously used to accelerate a reaction and enable a rapid and efficient treatment. Furthermore, when magnetized beads or magnetizable beads are used as the carrier particles, operations such as treatment of separating the supernatant from the beads, can be automatically, efficiently or quickly performed.

The method of immobilizing oligo (dT) onto a carrier is not particularly limited. However, fixing can be performed, for example, by a covalent bonding, ion bonding, physical adsorption, and biological binding (e.g., binding between biotin and avidin or streptoavidin, binding between antigen and antibody) and the like. Oligo (dT) may be fixed onto a career via a spacer sequence (e.g., a hydrocarbon group having 1 to 10 carbon atoms).

The fixing of oligo (dT) onto a carrier via a covalent bond can be performed by introducing a functional group into the oligo (dT) and introducing another functional group reactive with the aforementioned functional group to the surface of a carrier and then reacting the two functional groups. For example, when an amino group is introduced into oligo (dT), and an active ester group, epoxy group, aldehyde group, carbodiimide group, the isothiocyanate group or the isocyanate group is introduced into a carrier, a covalent bond can be formed. Alternatively, a covalent bonding may be formed by introducing a mercapto group into oligo (dT), and introducing an active ester group, maleimide group or disulphide group into a carrier. Examples of the active ester group include p-nitrophenyl group, N-hydroxy succinimide group, succinimide group, phthalimide group and 5-norbornene-2,3-dicarboximide group.

As a method of introducing a functional group into the surface of a carrier, a method of treating a carrier with a silane coupling agent having a desired functional group may be mentioned. Examples of the coupling agent include γ-aminopropyltriethoxysiolane, N-β-(aminoethyl)-γ-aminopropyltrimethoxysilane, N-β-(aminoethyl)-β-aminopropylmethyldimethoxysilane and γ-glycidoxypropyltrimethoxysilane. As another method of introducing a function group serving a binding site into a carrier, a plasma processing may be mentioned. By the plasma processing, a functional group such as a hydroxyl group or an amino group can be introduced into the surface of a solid phase. The plasma processing can be performed by use of an apparatus known to one skilled in the art.

To fix oligo (dT) onto a carrier by physical adsorption, an electrostatic binding method may be mentioned in which the oligo (dT) is fixed by means of its charge onto the surface of a carrier treated with polycation (such as polylysin, polyallylamine, polyethyleneimine).

The total number of oligo (dT) molecules fixed onto a carrier is preferably $10^{12}$ or more.

When particles are used as a carrier, the diameter of the particles is generally 50 µm or less. The total surface area of particles, on which oligo (dT) is to be fixed and hybridized with mRNA derived from a single-cell, is 0.1 cm² or more. A volume occupancy rate of the particles in its solution is preferably 1% or less. A number of particles to be used are preferably selected depending upon the number of oligo (dT) molecules fixed onto the particles and the diameters of the particles. When the number of oligo (dT) molecules to be fixed is about $5 \times 10^{12}/cm^2$ and the diameter of the particles is, in particular, 1.0 µm, the number of particles are preferably $10^7$ to $10^8$. When the diameter of particles is, in particular, 2.8 µm, the number of particles is preferably $10^6$ to $10^7$.

Since the total number of mRNA molecules present in a single-cell is $10^5$ to $10^6$, if $10^7$ particles larger than the number of mRNA molecules are used, at most one mRNA molecule is conceivably captured per particle. Since the number of oligo (dT) molecules to be fixed onto the surface of a single particle is quite large, even if reverse transcription is performed by use of a much smaller number of particles, the reverse transcription efficiency presumably may not decrease. Therefore, when quantitative analysis is performed by real-time PCR, as long as a reverse transcription efficiency may not decrease, cDNAs derived from a plurality of genes may be synthesized by capturing a plurality of mRNA molecules derived from a plurality of genes per particle on which a plurality of oligo (dT) molecules are fixed.

The reaction for hybridizing mRNA with oligo (dT) fixed on a carrier can be performed by incubating the oligo (dT) fixed carrier and a sample containing mRNA having a poly A sequence in a buffer. Such incubation for hybridization can be preferably performed at a temperature of 70° C. for about 5 minutes with gentle stirring, and thereafter, the temperature is reduced slowly to room temperature at a rate of about 0.1° C./second. As the buffer used herein, it is preferable to employ a buffer from which RNase activity is removed as much as possible. Furthermore, after the incubation, components not bound to the carrier are preferably washed away from the sample.

In the following step, reverse transcription of mRNA hybridized with oligo (dT) is performed to fix cDNA derived from a single-cell on a carrier, thereby preparing a single-cell derived cDNA library fixed onto a carrier. Synthesis of cDNA is performed by reacting oligo (dT) as a primer and the mRNA hybridized therewith as a template by use of a reverse transcriptase in the presence of deoxynucleotides (see FIG. 2).

After the reverse transcription, a carrier was washed with a buffer and the supernatant is removed. In this way, a residual reagent such as a cell lysis reagent and DNase can be removed and the following PCR amplification reaction can proceed without inhibition. Accordingly, the whole amount of cDNA sample derived from a single-cell can be used for analysis without dividing into portions. As a result, detection accuracy can be improved. When magnetic beads are used as a carrier, magnetic beads in a tube are captured by a magnet and the supernatant containing a residual reagent used in cDNA preparation is removed. Thereafter, the magnetic beads in the tube are suspended in a buffer, magnetic beads are captured by a magnet, and the supernatant is removed. Washing operation is performed in this way to easily prepare a library of single-cell derived cDNA fixed onto a carrier which is free from residual reagent.

Using the single-cell derived cDNA library fixed onto a carrier obtained in the aforementioned step, PCR is performed; at the same time the amplified amount is optically detected. In this way, cDNA derived from mRNA of a predetermined gene contained in a single-cell can be detected and quantified. Preferably, real-time PCR is performed using the single-cell derived cDNA library fixed onto a carrier.

The real-time PCR is a method for analyzing the amount amplified by PCR while monitoring it in real time. The real-time PCR is excellent in speed and quantification performance because it does not need electrophoretic analysis. In this method, a specialized real-time PCR apparatus having a thermal cycler and a spectrophotofluorometer integrated therein is generally used. First, PCR is performed using known amounts of DNA prepared by serial dilution as a standard. Based on this, the number of cycles (threshold cycle: Ct value) at which the amplification amount reaches a predetermined amount within the region where amplification takes place exponentially is obtained. The Ct value is plotted on the vertical axis and the initial amount of DNA (the number of DNA molecules) on the transverse axis to obtain a standard curve. A sample whose DNA concentration is unknown is subjected to PCR under the same conditions and the Ct value thereof is obtained. Based on the Ct value and the standard curve, the amount of desired DNA in the sample can be determined.

Now, an embodiment of a step for detecting an amplification amount while performing PCR of cDNA fixed onto a carrier will be explained below. In a carrier having cDNA, which is derived from a predetermined gene fixed thereto and present in the single-cell derived cDNA library fixed onto a carrier, a real-time PCR primer (R) present in a PCR solution is annealed with the cDNA derived from the predetermined gene. Thereafter, an elongation reaction of a complementary chain takes place to synthesize a PCR product (Reverse chain) complementary to the cDNA. Further heat denaturation is applied and thereafter, the aforementioned reaction is repeated; at the same time, a real-time PCR primer (F) present in the PCR solution is annealed with the PCR product (Reverse chain) thus produced. Subsequently, the elongation reaction of the complementary chain takes place to produce a PCR product (Forward chain). Likewise, in the initial PCR cycle, PCR reaction proceeds using the cDNA molecule fixed onto the carrier as a template. In the following PCR reaction, a reaction site moves to a liquid phase in which a real-time PCR primer (R) and a real-time PCR primer (F) are annealed with the PCR product (Forward chain) and PCR product (Reverse chain) respectively to produce PCR products. In this way, the PCR products are produced exponentially and accumulated in the liquid phase.

In the real-time PCR, detection of an amplification amount (detection of PCR product) can be performed by a method commonly used in the art such as an intercalator method and a fluorescent probe method. In the intercalator method, a reagent (such as an intercalator: SYBR (registered trademark) Green I) emitting fluorescence, when it binds to double stranded DNA, is added to a PCR reaction system. The intercalator binds to a double stranded DNA synthesized by a PCR reaction and emits fluorescence in response to irradiation of excitation light. When the intensity of the fluorescence is detected, the amount of the amplified product can be monitored. Also, a melting temperature of amplified DNA can be measured. In the fluorescent probe method, an oligonucleotide (a gene-specific probe), whose 5' end is modified with a fluorescent substance (such as FAM) and whose 3' end is modified with a quencher substance (such as TAMRA), is added to a PCR reaction system. The fluorescent probe is specifically hybridized with a temperate DNA in an annealing step. However, a quencher is present on the probe. Therefore, even if excitation light is applied, generation of fluorescence is suppressed. In an elongation reaction step, when the gene-specific probe hybridized with the temperate is degraded by 5'→3' exonuclease activity of Taq DNA polymerase, a fluorescent dye is liberated from the probe. Since suppression by the quencher is released in this manner, fluorescence is emitted. When the intensity of fluorescence is measured, the amount of amplified product can be monitored. In the nucleic acid detection method of the present invention, the fluorescent probe method is preferably employed.

Although emission of fluorescence is weak, background noise can be suppressed to a low level by the fluorescent probe method in which non-specific fluorescence is virtually not emitted compared to the fluorescence-emitting intercalator method involving non-specific fluorescence emission. Therefore, in the fluorescent probe method measurement can be performed with high sensitivity (higher S/N ratio). For the reason, the fluorescent probe method is suitable when an extremely small amount of nucleic acid derived from a single-cell is determined.

The nucleic acid detection method of the present invention according to another embodiment, further comprises, after a step of amplifying cDNA fixed onto the carrier and simultaneously detecting an amplification amount of the cDNA, a step a of recovering and washing a carrier and step b of amplifying the cDNA fixed onto the carrier and simultaneously detecting the amplified amount. In this embodiment, expression analysis of the gene is carried out by performing an amplification reaction of cDNA derived from a specific gene and detecting amplified amount and thereafter, the carrier is recovered and washed, and then, reused as a single-cell derived cDNA library fixed onto a carrier. The single-cell derived cDNA library fixed onto a carrier can be repeatedly used as an analysis sample by the washing operation. Thus, the same single-cell derived cDNA library fixed onto a carrier can be used for determining the number of cDNA molecules (corresponding to the number of copies of mRNA molecules) derived from various genes in a same cell.

The nucleic acid detection method of the present invention according to another embodiment, further comprises, after the step b, a step of repeating the step a and the step b. In this embodiment, the step a and step b are repeated a number of times, which correspond to the number of genes to be analyzed for expression amount. Therefore, the number of times of repeating the steps a and b is not particularly limited and appropriately set in accordance with the number of desired genes.

According to the present invention, it is possible to easily purify and recover a small amount of cDNA at a single-cell level, which is considered difficult to attain by a conventional method, by preparing a single-cell derived cDNA library fixed onto a carrier. Furthermore, it is possible to remove a residual reagent (such as cell lysis reagent and DNase reagent), which remains in a sample by conventional methods. Therefore, PCR inhibition with the residual reagent cannot be taken into consideration, and a whole amount of cDNA sample derived from a single-cell can be used in an amplification reaction without dividing the cDNA sample into portions. More specifically, Real Time PCR analysis can be performed with a higher sensitivity than those of the conventional methods. Moreover, since a sample is used up when every time analysis is made in conventional methods, the number of genes that can be analyzed is limited when using an extremely small amount of cDNA derived from a single-cell. However, since the single-cell derived cDNA library fixed onto a carrier can be reused as a PCR analysis sample repeatedly by washing, the expression amounts of a wide variety of genes in a same cell can be analyzed.

The nucleic acid detection method using a single-cell derived cDNA library fixed onto a carrier prepared by immobilizing cDNA derived from a single-cell, as an analysis sample, can be used as a nucleic acid detection method using a library of a cDNA fixed onto carrier prepared by immobilizing cDNA derived from a plurality of cells and directed to a plurality of cells as an analysis material. In particular, this method can be advantageously used to a small number of cells. When a small number of cells in the order of $10^3$ or less are used as analysis samples, conventional expression analysis methods have problems: sensitivity is low and measurement error is large. In contrast, if the method of the present invention is employed, quantitative analysis can be made highly accurately even though a small number of cells are used.

More specifically, the present invention according to an embodiment, comprises a step of sampling a plurality of cells as large as $10^3$ or less from a sample containing cells, a cell lysis step of lysing cell membrane of the sampled cells and extracting nucleic acids from the cells, a DNase treatment step of degrading DNA of the extracted nucleic acids with DNase, a step of hybridizing mRNA of the total RNA contained in the cells with oligo (dT) fixed onto a carrier, a step of performing a reverse transcription of the mRNA hybridized with oligo (dT) to fix cDNA derived from the cells onto the carrier, thereby preparing a library of a cDNA fixed onto a carrier, and a step of amplifying cDNA fixed onto the carrier and simultaneously detecting an amplification amount of the cDNA.

Now, the present invention will be more specifically described by way of Examples, which will not be construed as limiting the invention.

EXAMPLES

A plurality of genes was previously selected as analysis objects. How many cDNA molecules were derived from mRNA of each genes and present in a single-cell, which was used as an analysis sample, was determined in accordance with the operations from Step 1-1 to Step 1-6 shown in the flowchart of FIG. 1. To explain more specifically, first a single-cell was sampled (Step 1-1). Subsequently, the cell was lysed (Step 1-2). Genomic DNA of the single-cell was removed by DNase treatment (Step 1-3). Reverse transcription was performed using a carrier having oligo (dT) fixed thereon to prepare a single-cell derived cDNA library fixed onto a carrier (Step 1-4). To improve cDNA synthesis efficiency and minimize variation between samples in preparing the library of the single-cell derived cDNA fixed onto a carrier, Step 1-1 to Step 1-4 were performed in a single tube. Using the library of the single-cell derived cDNA fixed onto a carrier, real-time PCR was performed to determine the expression amount of a desired gene to be analyzed in the single-cell (Step 1-5). The library of the single-cell derived cDNA fixed onto a carrier was recovered and washed (Step 1-6). In this manner, the library of the single-cell derived cDNA fixed onto a carrier was reused as an analysis sample for determining the expression amounts of a plurality of genes. Each of the steps will be more specifically explained below.

<Single-Cell Sampling>

In a first place, to sample a single-cell as shown in Step 1-1 of FIG. 1, human colon cancer cells (HCT116) provided by the American Type Culture Collection (ATCC) were suspended in an appropriate amount of Advanced D-MEM culture solution (manufactured by GIBCO) containing 5% of glutamine and 10% of inactivated fetal bovine serum. The suspension was placed in a sterilized flask and cultured at 37° C. in a 5%-$CO_2$ atmosphere for 1 to 2 days. It was microscopically confirmed that no microbial contamination took place and cells were proliferated without problems. Subsequently, cultured cells attached onto the bottom of the sterilized flask were washed with 3 mL of a phosphate buffer (pH 7.4, manufactured by GIBCO). 1 mL of trypsin (manufactured by GIBCO) was added to the flask and incubation was performed at 37° C. for 3 minutes. The cells were exfoliated and suspended. To inactivate trypsin in the cell suspension, 3 mL of Advanced D-MEM culture solution containing 5% of glutamine and 10% of inactivated fetal bovine serum was added. The cell suspension (about 4 mL) was transferred to a 15 mL tube and centrifuged at 1000 rpm for 3 minutes at 4° C., and thereafter, the supernatant was removed. Cell mass collected at the bottom of the 15 mL tube was suspended with about 10 mL of a phosphate buffer (pH 7.4). The number of cells was counted by a hemocytometer (Burker-Turk type). The number of cells countable by the hemocytometer is about $10^5$ to $10^7$/mL. Therefore, after counting cells, the cell suspension was further diluted to a concentration of about 500 cells/mL. 100 μL of the diluted cell suspension (i.e., containing about 50 cells) was transferred to a recess (having an area of 2 $cm^2$) of a cover of a 96-well plate (manufactured by FALCON) to form liquid drops. Subsequently, a single-cell was suctioned together with 1 μL of a phosphate buffer (pH 7.4) by means of a pipette (having a tip diameter of 190 μm, manufactured by Drummond) under microscopic observation (magnification: 100 times). When the cell was discharged abruptly, the cell would be broken. Therefore, 1 μL of a phosphate buffer (pH 7.4) was previously placed at the bottom of a PCR tube (low adsorbable tube, manufactured by Axygen Scientific) and the tip of the pipette was inserted into the phosphate buffer, and then, the single-cell was gently discharged. In the same manner, 6 single-cell samples (i.e., containing a single-cell in 2 μL of the phosphate buffer) and a negative control sample (i.e., containing no cell in 2 μL of the phosphate buffer) were prepared. To avoid RNA degradation, the cell samples thus picked up were placed on ice and the next operation was quickly carried out.

<Cell Lysis>

First, 8 μL of Resuspension Buffer and 0.8 μL of Lysis Enhancer supplied attached to SuperScript III CellsDirect cDNA Synthesis System (manufactured by Invitrogen) were mixed to prepare a reagent mixture for cell lysis. The reagent mixture was dispensed to individual tubes containing a sample by 1.1 μL and treated with heat at 75° C. for 10 minutes to lyse cells (Step 1-2 of FIG. 1).

<DNase Treatment>

To degrade a genomic DNA contained in a sample, after the sample was placed on ice and cooled for 3 minutes, 4.0 μL of DNase I (1 U/μL, manufactured by Invitrogen) and 2.88 μL of 10 X DNase I Buffer were mixed to prepare a reagent mixture for DNase treatment, and the reagent mixture was dispensed to individual tubes containing a sample by 0.86 μL and incubated at room temperature for 5 minutes. After completion of the reaction, 1.2 μL of 2.5 mM EDTA was added to the individual tubes containing a sample. Then the resultant mixture was treated with heat at 70° C. for 5 minutes to inactivate DNase I (step 1-3 of FIG. 1).

<Fixing of Oligo $(dT)_{30}$ Onto the Surface of Magnetic Beads>

Oligo $(dT)_{30}$ (SEQ ID NO: 1) was fixed onto magnetic beads by the following operation. Magnetic beads (diameter: 1 μm, $10^7$ particles/μL, manufactured by DYNAL BIOTECH) whose surface was coated with streptoavidin were suspended well until a uniform concentration was obtained. Then, 100 μL of the suspension (containing $10^9$ magnetic beads) was collected and transferred to a 1.5 mL tube. A magnet was placed near the 1.5 mL tube to capture magnetic beads and the supernatant was removed. Furthermore, 100 µL of Binding & Washing Buffer (5 mM Tris-HCl (pH 7.5), 0.5 mM EDTA, 1 M NaCl) was mixed with the magnetic beads. After the magnetic beads were captured by a magnet, the supernatant was removed. In this way, the magnetic beads were washed. The washing operation was repeated three times. Subsequently, to 6.67 µL of the oligo $(dT)_{30}$ (100 pmol/µL) having the 5' end modified with 2 biotin molecules and containing 6 carbon atoms as a spacer sequence, Binding & Washing Buffer was added to prepare 400 µL (1.67 pmol/µL, $4.0 \times 10^{14}$ molecules) of an oligo $(dT)_{30}$ diluted solution. 400 µL of the oligo $(dT)_{30}$ diluted solution was added to the magnetic beads washed above. The resultant mixture was stirred well for 60 minutes by a rotor. Using streptoavidin-biotin binding, the oligo $(dT)_{30}$ was bonded to the surface of the magnetic beads. To remove excess oligo $(dT)_{30}$, which failed to bind to the magnetic beads, the supernatant was removed while capturing the magnetic beads by a magnet, and the magnetic beads were washed twice with Binding & Washing Buffer. Furthermore, to remove RNase, the magnetic beads were washed twice with a solution A (0.1N NaOH, 0.05M NaCl, treated with DEPC) and once with a solution B (0.1M NaCl, treated with DEPC). Thereafter, 200 µL of sterilized water was added to prepare a suspension of magnetic beads having oligo $(dT)_{30}$ fixed thereon ($0.5 \times 10^7$ molecules/µL, the estimated number of oligo $(dT)_{30}$ molecules: about $2.0 \times 10^5$/magnetic bead).

<Reverse Transcription of mRNA Performed on the Surface of Magnetic Beads>

Figure 2:
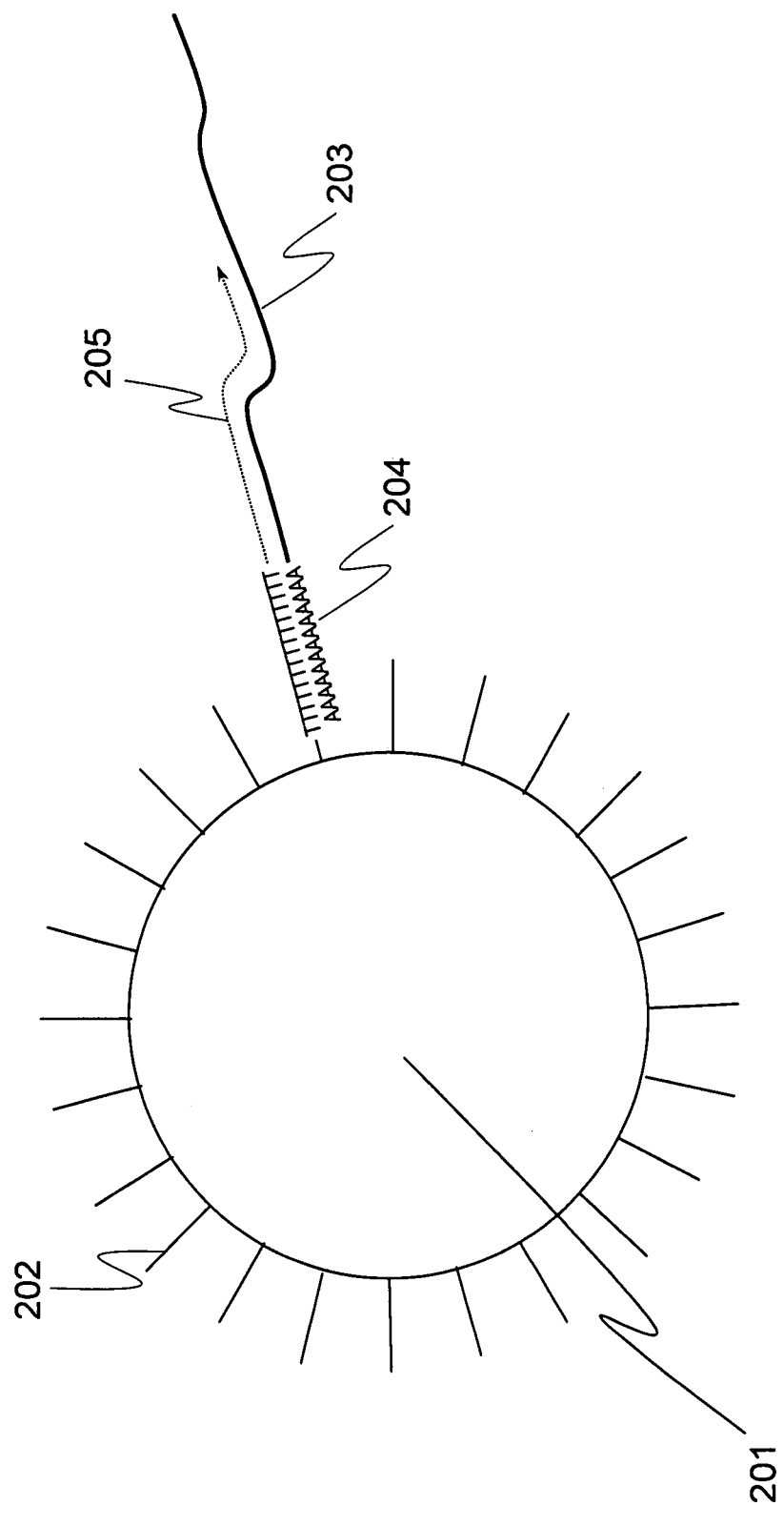
FIG. 2 shows an embodiment of the mRNA reverse transcription performed on the surface of a carrier in the present invention.

First, 16 µL of the magnetic beads suspension having oligo $(dT)_{30}$ fixed thereon ($0.5 \times 10^7$ molecules/µL) prepared above, 8 µL of dNTP Mix (10 mM each) and 124.8 µL of a 0.1% Tween solution were mixed. The obtained mixture was dispensed to individual tubes containing a sample by 18.6 µL each (containing $10^7$ of magnetic beads) and treated with heat at 70° C. for 5 minutes and then cooled to 4° C. As a result, the poly A sequence (204) present at the 3' end of mRNA (203) was hybridized with the oligo $(dT)_{30}$ (202) fixed onto the magnetic bead (201) as shown in FIG. 2. Subsequently, 48 µL of 5×RT Buffer, 8 µL of DTT (0.1 M), 8 µL of RNase OUT (40 U/µL) and 8 µL of Super Script III RT (200 U/µL) was mixed and obtained mixture was dispensed to individual tubes containing a sample by 9 µL each. The resultant was treated with heat at 50° C. for 50 minutes and then 85° C. for 5 minutes, and cooled to 4° C. to obtain about 33 µL of a cDNA solution (Step 1-4 of FIG. 1). More specifically, as shown in FIG. 2, cDNA (205) was synthesized from mRNA (203) as a template by a reverse transcription performed on the surface of the magnetic bead. After completion of the reverse transcription, the supernatant containing a residual reagent required for cDNA preparation was removed while capturing the magnetic beads of individual tubes by a magnet. Furthermore, the magnetic beads in each of the tubes were suspended in 100 µL of Tris-HCL (10 mM, pH 7.5). After the magnetic beads were captured by a magnet, the supernatant was removed. This washing operation was repeated twice. In this way, a single-cell derived cDNA library fixed onto magnetic beads (magnetic beads: $10^7$) was obtained. Since reverser transcription of all mRNA molecules ($10^5$ to $10^6$) present in a single-cell were performed by use of magnetic beads ($10^7$) of larger number than the molecular number of mRNA, at most one mRNA molecule was captured by a single magnetic bead and subjected to reverse transcription.

Figure 3:
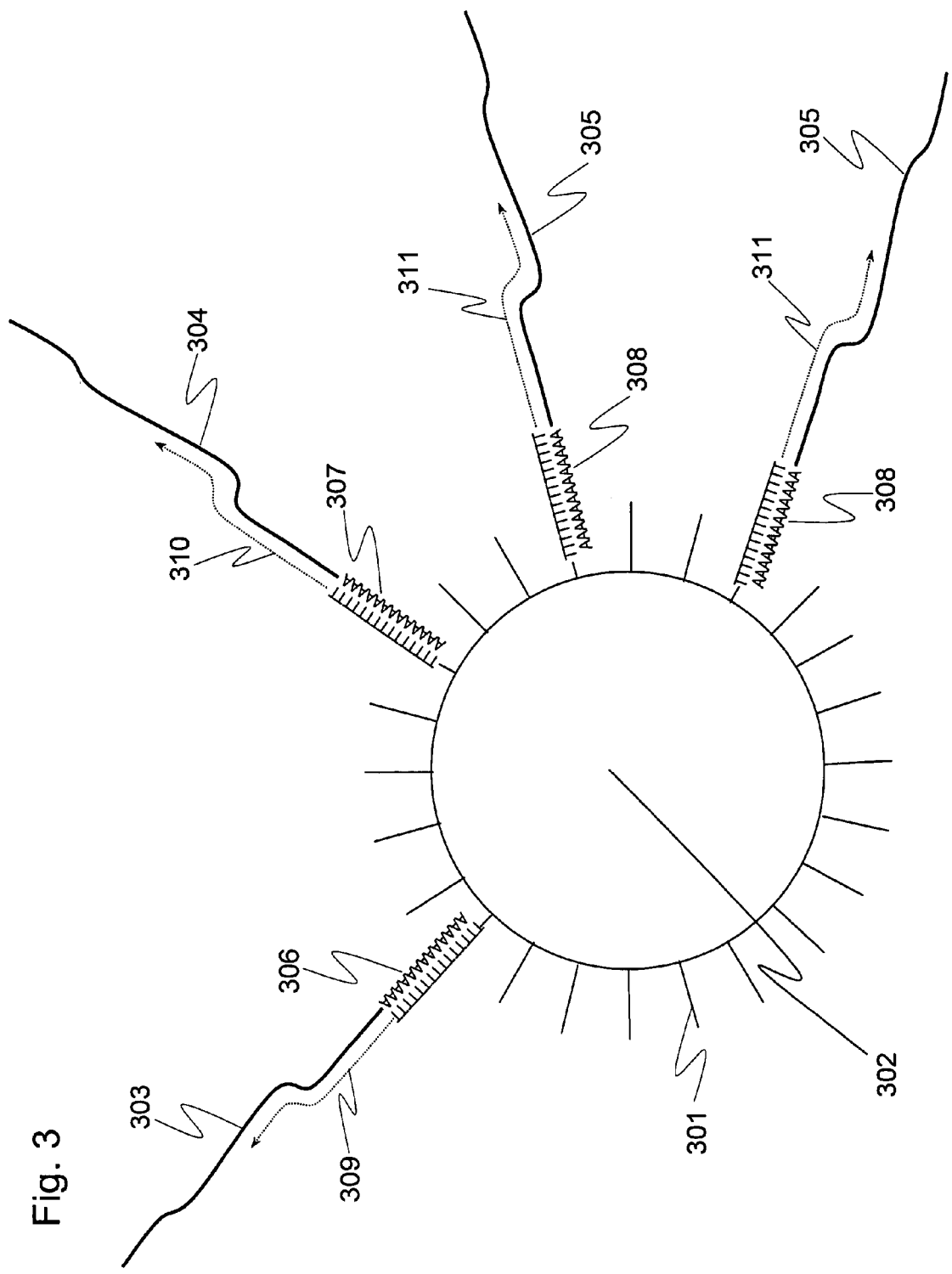
FIG. 3 shows an embodiment of the mRNA reverse transcription performed on the surface of a carrier according to the present invention.

The number of oligo $(dT)_{30}$ molecules (202) to be fixed onto the surface of a single magnetic bead is as large as about $2 \times 10^5$. Therefore, even if reverse transcription is performed by use of a smaller number of magnetic beads than $10^7$, the efficiency of the reverse transcription is estimated not to decrease. Thus, when quantitative analysis is performed by real-time PCR, as long as the efficiency of reverse transcription is not lowered, the approach shown in FIG. 3 may be performed. That is, to a single magnetic bead (302) having about $2 \times 10^5$ oligo $(dT)_{30}$ molecules (301) fixed thereon, a single mRNA molecule derived from gene A (303), a single mRNA molecule derived from gene B (304), and two single mRNA molecules derived from gene C (305) can be bound by hybridizing each of the poly A sequences (306, 307, 308) with the oligo (dT) 30 (301) molecules, thereby synthesizing a single cDNA molecule derived from gene A (309), a single cDNA molecule derived from gene B (310), and two cDNA molecules derived from gene C (311).

<Preparation of a Standard Sample for Preparing b2M Standard Curve>

Real-time PCR was performed to determine how many cDNA molecules derived from b2M gene were present in a single-cell derived cDNA library fixed onto magnetic beads ($10^7$ of magnetic beads). First, a known number of DNA having b2M gene sequence (PCR product) were fixed onto the surface of magnetic beads. Then, a standard sample for obtaining a standard curve of real-time PCR was prepared as follows.

In the same manner of immobilizing oligo $(dT)_{30}$ onto magnetic beads as mentioned above, magnetic beads (diameter: 1 µm, $10^7$ particles/µL, manufactured by DYNAL BIOTECH) whose surface was coated with streptoavidin were suspended well until a uniform concentration was obtained. Then, 50 µL of the suspension containing $5 \times 10^8$ magnetic beads was collected and transferred to a 1.5 mL tube. A magnet was placed near the 1.5 mL tube to capture magnetic beads and the supernatant was removed. Furthermore, 50 µL of Binding & Washing Buffer was mixed with the magnetic beads. After the magnetic beads were captured by a magnet, the supernatant was removed. In this way, the magnetic beads were washed. The washing operation was repeated three times and thereafter the magnetic beads were suspended with 50 µL of Binding & Washing Buffer. Subsequently, b2M gene was amplified by PCR using a PCR primer set (SEQ ID NOS: 2 and 3) (the (R) primer had the 5' end modified with 2 biotin molecules) for preparing a standard template. The PCR primer set was positioned at the outer side of a real-time PCR primer set (SEQ ID NOS: 10 and 11). Through the amplification, a b2M-PCR product of 264 bp (the 5' end of the Reverse chain was modified with 2 biotin molecules) was obtained. The b2M-PCR product was diluted with Binding & Washing Buffer to a concentration of $10^6$ molecules/µL to obtain b2M-PCR product solution. 50 µL of the b2M-PCR product solution was divided into 10 portions of 5 µL and individual portions were separately added to 50 µL of magnetic beads while mixing. The mixture was stirred by a shaker at 600 rpm for 60 minutes at room temperature. Using streptoavidin-biotin binding, the b2M-PCR product was fixed onto the surface of the magnetic beads (100 µL in total). To remove the b2M-PCR product failing to bind to magnetic beads, the magnetic beads were captured by a magnet and the supernatant was removed. The magnetic beads were washed three times with 100 µL of Binding & Washing Buffer. The amounts of residual b2M-PCR product in the supernatant and washing solution were checked by real-time PCR and confirmed that substantially the whole amount of PCR products were fixed onto the surface of magnetic beads. Furthermore, an attempt was made to obtain a single stranded b2M-PCR product by washing the magnetic beads having the b2M-PCR product fixed thereto with 50 µL of NaOH (0.1 M). By virtue of this operation, only the Reverse chain of the b2M-PCR product having two biotin molecules attached thereto was fixed onto the magnetic beads and the Forward chain of the b2M-PCR product was removed. Subsequently, the magnetic beads were washed twice with 50 µL of Tris-HCl (10 mM, pH 7.5) and then suspended in 50 µL of the same solution to obtain a standard sample containing b2M-PCR product Reverse chain (single stranded DNA) in a concentration of $10^6$ molecules/µL (magnetic beads concentration: $10^7$/µL). Un-fixed magnetic beads (washed beads, $10^7$/µL) were serially diluted 10 folds to prepare standard dilution series A having magnetic beads in a constant concentration ($10^7$/µL) and having template (b2M-PCR product Reverse chain) in concentrations from $10^6$ molecules/µL to $10^1$ molecules/µL. In the same manner, $10^6$/µL of the b2M-PCR product Reverse chain not fixed onto magnetic beads was diluted with Tris-HCl (10 mM, pH7.5) to prepare standard dilution series B having temperate concentrations from $10^6$ molecules/µL to $10^1$ molecules/µL.

<Real-Time PCR Measurement of the b2M Derived cDNA Molecule>

Sequentially, 80 µL of 2× TaqMan Universal PCR Master Mix (manufactured by ABI), 16 µL of each of 10 µM real-time PCR primer (F) (SEQ ID NO: 10) and 10 µM real-time PCR primer (R) (SEQ ID NO: 11) and further 16 µL of a 2.5 µM gene-specific probe (SEQ ID NO: 18) and 32 µL of 0.1% Tween solution were mixed on ice to prepare a PCR solution A. This PCR solution A was dispensed to each of samples of a single-cell derived cDNA library fixed magnetic beads (magnetic beads: $10^7$) by 20 µL each, and stirred well to prepare reaction solutions, which was each transferred to a 384-well microplate. Furthermore, 390 µL of 2× TaqMan Universal PCR Master Mix (manufactured by ABI), 78 µL of each of 10 µM real-time PCR primer (F) (SEQ ID NO: 10) and 10 µM real-time PCR primer (R)(SEQ ID NO: 11), and further 78 µL of a 2.5 µM gene-specific probe (SEQ ID NO: 18) and 117 µL of 0.1% Tween solution were mixed on ice to prepare PCR solution B. This PCR solution was dispensed by 19 µL to the wells of a 384-well microplate. To each of the wells, standard dilution series A and standard dilution series B were added by 1 µL each as a template. To obtain an accurate standard curve, each of the standard dilution series were measured three times (n=3). The 384-well microplate having each reaction solution added thereto was closed airtight with an optical detection seal, denatured with heating at 95° C. for 10 minutes and thereafter subjected to a cycle consisting of 95° C. for 15 seconds→60° C. for one minute. This cycle was repeated 50 times. Fluorescence was detected from the PCR product in each amplification cycle.

Figure 4:
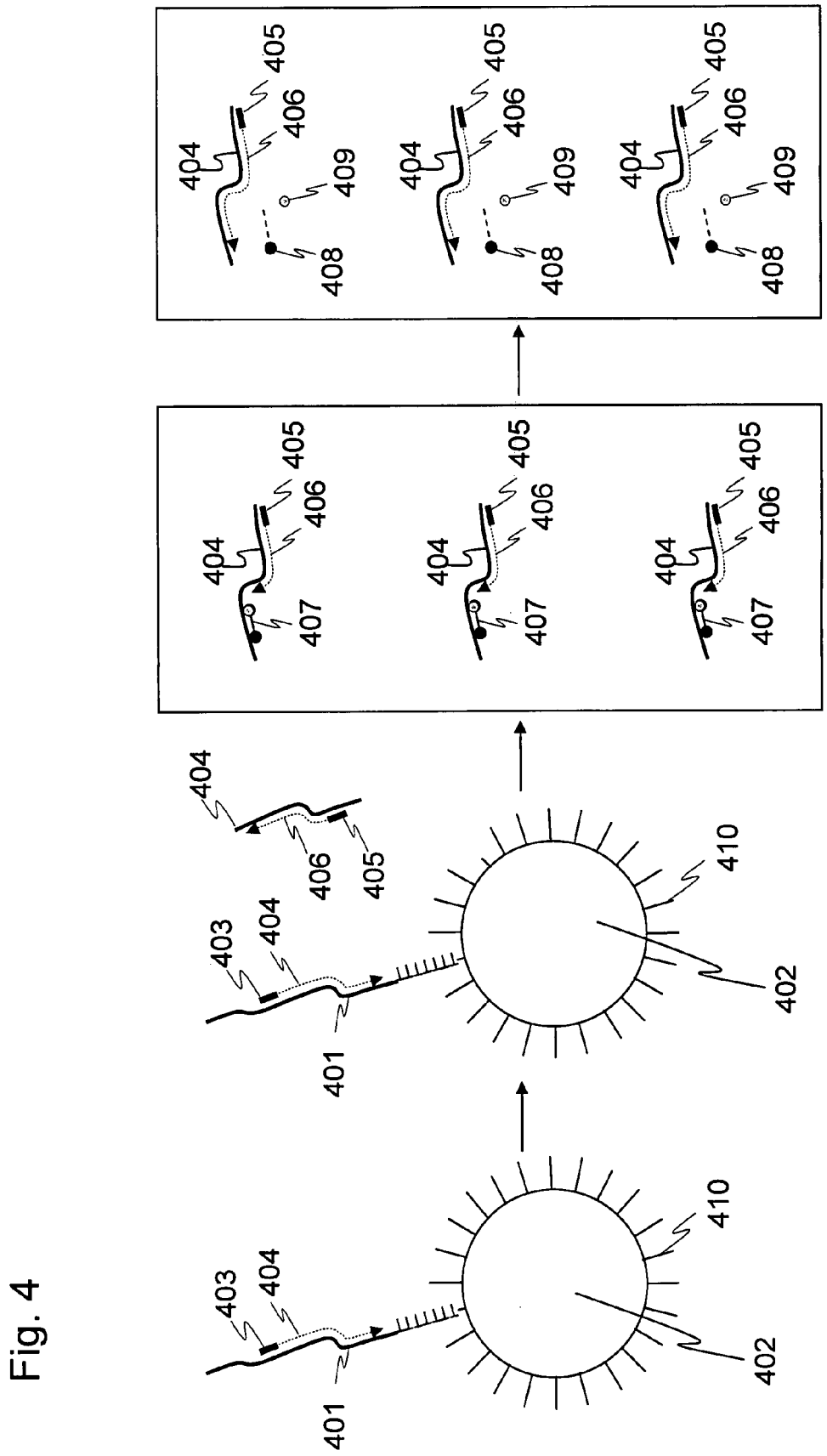
FIG. 4 shows an embodiment of real-time PCR according to the present invention.

An embodiment of the real-time PCR of the present invention is shown in FIG. 4. In a magnetic bead (402) having a b2M-cDNA molecule (401) fixed thereto and present in a sample of a single-cell derived cDNA library fixed magnetic beads ($10^7$ magnetic beads), first, b2M real-time PCR primer (R)(403) present in a PCR solution is annealed with the b2M-cDNA (401). 410 represents the oligo (dT)$_{30}$ fixed on the magnetic beads. Thereafter, a complementary chain elongation reaction takes place to synthesize a PCR product (Reverse chain)(404) complementary to the b2M-cDNA (401). After heat denaturation, the aforementioned reaction is repeated; at the same time, the real-time PCR primer (F) (405) present in the PCR solution is annealed with the PCR product (Reverse chain) (404) thus generated, and complementary chain elongation reaction proceeds to produce a PCR product (Forward chain) (406). Likewise, in the initial PCR cycle, the reaction proceeds using the b2M-cDNA molecule (401) fixed onto a magnetic bead as a template. The following PCR proceeds in a liquid phase. More specifically, to the PCR product (Reverse chain) (404) and PCR product (Forward chain) (406), the real time PCR primer (F) (405) and real-time PCR primer (R) (403) are annealed, respectively. The PCR product is produced exponentially and accumulated in the liquid phase. Subsequently, a b2M gene specific probe (407) is hybridized with the PCR product (Reverse chain) (404). At the same time, a real-time PCR primer (F) (405) is annealed with the 3' end of the PCR product (Reverse chain) (404). Then, the elongation reaction proceeds. Since the 3' end of the b2M gene-specific probe (407) is modified with a quencher and a Tm temperature regulation molecule, whereas the 5' end thereof is modified with a fluorescent substance (FAM), a fluorescence signal is not detected at it is. However, in the elongation reaction, DNA synthetase syntheses a complementary chain while breaking the b2M gene specific probe (407). Therefore, a fluorescent substance (409) is liberated from a broken b2M gene specific probe (408) and a fluorescence signal can be detected. In brief, a fluorescence signal having intensity proportional to the number of PCR products can be detected.

<Quantitative Analysis for the Number of cDNA Molecules Derived from mRNA of b2M>

Figure 5:
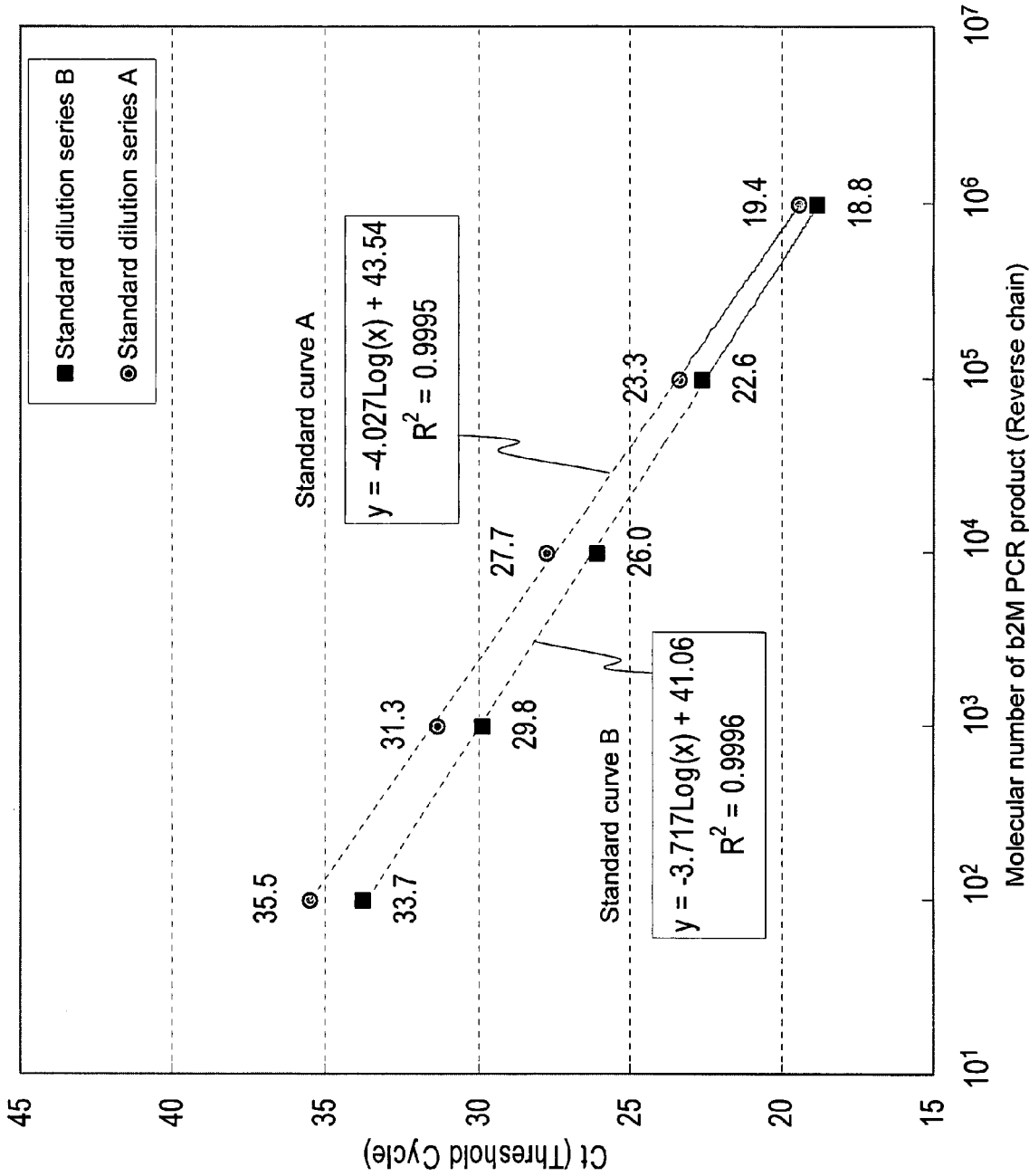
FIG. 5 shows a graph, in which the molecular number of templates in a sample for a standard curve is plotted on the transverse axis and a Ct value on the vertical axis, showing standard curves in a real-time PCR. The inclination of a standard curve approximation formula indicates PCR amplification efficiency and R$^2$ value indicates the degree of quantification accuracy.
Figure 6:
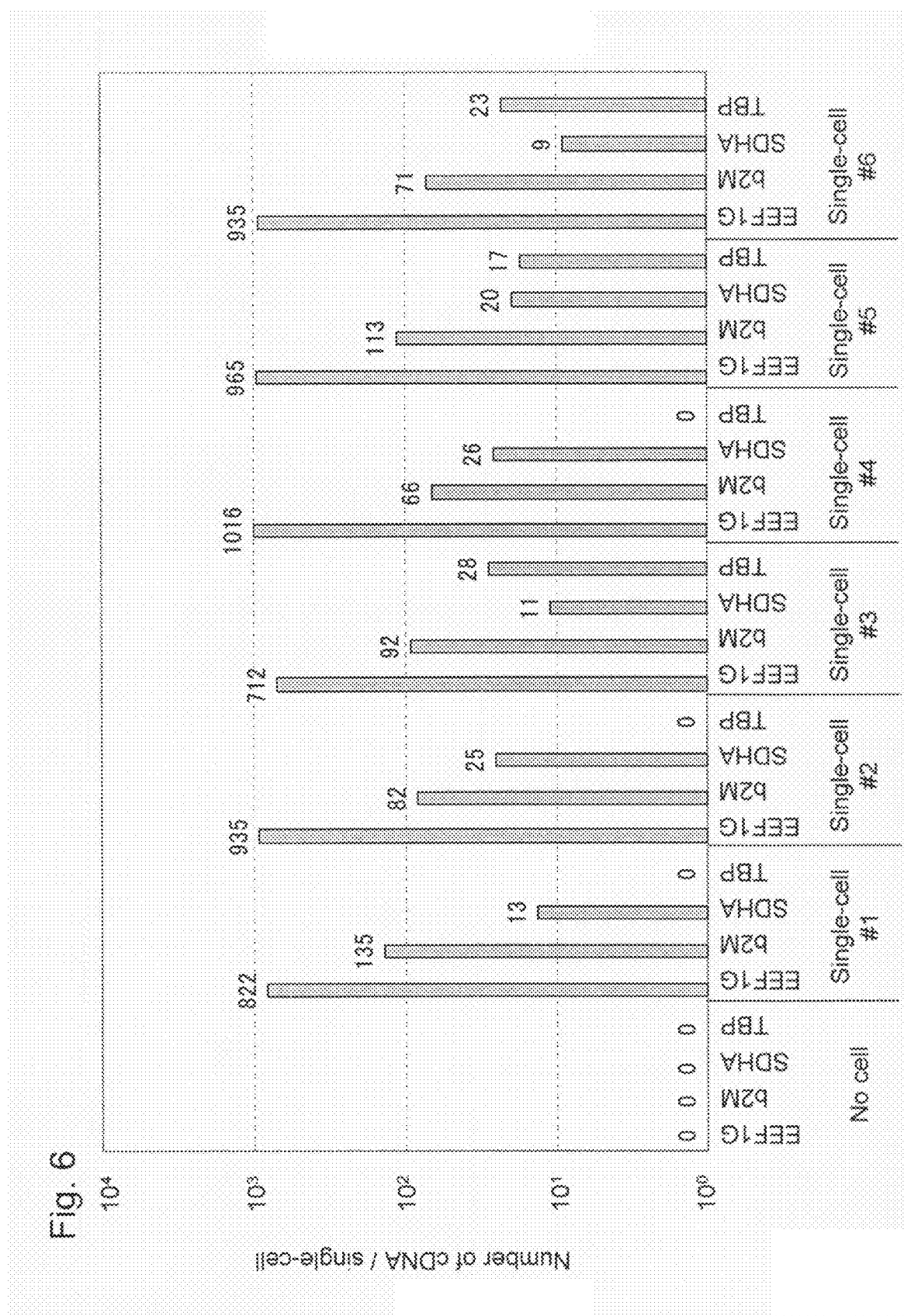
FIG. 6 shows the calculation results indicating the number of cDNA molecules (corresponding to the number of copies of mRNA molecules) encoding 4 types of genes contained in a negative control (0 cell) and single-cell samples (n=6). The number of cDNA molecules is calculated by plotting a Ct value, which is obtained from a sample of a single-cell derived cDNA library fixed onto magnetic beads, on a standard curve of a standard dilution series.

Using attached analysis software SDS ver.2.1, a Ct value of each of amplification curves (which is an S letter curve obtained by plotting a fluorescent value on the vertical axis and the number of PCR cycles on the transverse axis) was calculated. The Ct value represents the number of PCR cycles at the time the yield of a PCR product reaches to a threshold. FIG. 5 shows a graph showing standard curves each obtained by plotting the number of templates contained in a sample for a standard curve on the transverse axis and plotting a Ct value on the vertical axis. Compared to the standard curve of standard dilution series B, in which templates are not fixed (that is, containing no magnetic beads) which has an inclination of −3.717, that of standard dilution series A, in which templates are fixed onto the surface of magnetic beads, has an inclination of −4.027. As is apparent from this, a PCR amplification efficiency of standard dilution series A slightly decreases; however, $R^2$ value thereof is as high as 0.9995. From this, it is confirmed that quantification performance is not damaged. Hence, it is demonstrated that real-time PCR is suitable as a means for quantifying the number of templates fixed onto the surface of magnetic beads ($10^7$). By plotting a Ct value obtained from a sample of a single-cell derived cDNA library fixed onto magnetic beads ($10^7$ magnetic beads) on the standard curve of standard dilution series A, the number of cDNA (corresponding to the number of copies of mRNA) encoding a b2M gene contained in a single-cell is calculated (FIG. 6).

<Quantitative Analysis of cDNA Derived from Other Genes Fixed Onto Magnetic Beads>

Reusing the same sample of a single-cell derived cDNA library fixed onto magnetic beads (magnetic beads: $10^7$), the numbers of cDNA derived from mRNA of other genes per single-cell were determined (that is, the step 1-6 and step 1-5 of FIG. 1 were repeated).

First, in the same manner as in a b2M gene as mentioned above, PCR amplification of each of the genes was performed by use of standard template preparation PCR primer set for each gene (the 5' end of the (R) primer is modified with two biotin molecules). That is, the primer set for EEF1G: SEQ ID NOS: 4 and 5, the primer set for SDHA: SEQ ID NOS: 6 and 7, and the primer set for TBP: SEQ ID NOS: 8 and 9 were used. Each of the PCR products was fixed onto the surface of magnetic beads by use of streptoavidin-biotin binding. Subsequently, the PCR product was separated into single strands with NaOH (0.1M). In this way, a standard dilution series containing magnetic beads in a constant concentration of $10^7/\mu L$ and a PCR Reverse-chain template in a concentration of $10^6$ molecules/$\mu L$ to $10^1$ molecules/$\mu L$ was prepared with respect to each PCR product.

After the first real-time PCR for measuring cDNA of a b2M gene was performed, a magnet was placed near a reaction solution containing a sample of a single-cell derived cDNA library fixed onto magnetic beads (magnetic beads: $10^7$) to capture the magnetic beads and the supernatant was removed. Subsequently, the magnetic beads were suspended in 40 µL of a 0.1% Tween solution. After the magnetic beads were captured by a magnet, the supernatant was removed. This operation was repeated twice. In this manner, b2M gene specific probe (SEQ ID NO: 18), real-time primer sets (F) (R) (SEQ ID NOS: 10 and 11), and PCR products contained in the sample of a single-cell derived cDNA library fixed onto magnetic beads were removed (Step 1-6 of FIG. 1). Using the sample of a single-cell derived cDNA library fixed onto magnetic beads washed, a standard dilution series of EEF1G as a template, a real-time PCR primer set for EEF1G (EEF1G: SEQ ID NOS: 12 and 13), and a gene-specific probe (EEF1G: SEQ ID NO: 19), a second real-time PCR quantitative analysis was performed. In the same manner as performed after the first real-time PCR, using the sample of a single-cell derived cDNA library fixed onto magnetic beads washed with a 0.1% Tween solution, a standard dilution series of SDHA as a template, real-time PCR primer set for SDHA (SDHA: SEQ ID NOS: 14 and 15), and a gene-specific probe (SDHA: SEQ ID NO: 20), a third real-time PCR quantitative analysis was performed. Subsequently, using the sample of a single-cell derived cDNA library fixed onto magnetic beads washed with a 0.1% Tween solution, a standard dilution series of TBP as a template, a real-time PCR primer set for TBP (TBP: SEQ ID NOS: 16 and 17), and a gene-specific probe (TBP: SEQ ID NO: 21), a fourth real-time PCR quantitative analysis was performed.

A standard curve was obtained by plotting the number of template molecules contained in a standard dilution series on the transverse axis and a Ct value on the vertical axis. The Ct value obtained from the sample of a single-cell derived cDNA library fixed onto magnetic beads washed (magnetic beads: $10^7$) was plotted on the standard curve. In this manner, the numbers of cDNA molecules (corresponding to the numbers of copies of mRNA molecules) contained in a single-cell were also calculated with respect to three genes, namely, EEF1G, SDHA and TBP genes (FIG. 6). With respect to 6 single-cell samples, the numbers of cDNA molecules (corresponding to the numbers of copies of mRNA molecules) per single-cell are compared with respect to the 4 genes analyzed. As a result, EEF1G shows the largest number (about 1000 copies/cell) as is apparent from the graph of FIG. 6. The number of copies decreases sequentially in the order of b2M, SDHA, and TBP. Furthermore, it is confirmed that no fluorescent signal is detected from a negative control of each gene sample containing no cells. To confirm reliability of the results obtained from single-cell samples, the number of cDNA molecules (corresponding to the number of mRNA molecules) contained in a sample (a 10-cell sample and a 1000-cell sample) was quantitatively determined in the same manner as shown in Steps 1-1 to 1-6 of FIG. 1. The results are shown in Table 7. With respect to the TBP gene whose expression is low, linearity is low, meaning that quantitativeness is slightly low. However, it is confirmed that as to other three genes: b2M, EEF1G and SDHA genes, high quantitativeness was shown.

<Confirmation of Usefulness of a Single-Cell Derived cDNA Library Fixed Onto Magnetic Beads (Based on Study on PCR Inhibition by Residual Reagent)>

Although cDNA can be prepared by a conventional method using no magnetic beads and comprising a cell lysis step, DNase treatment step and reverse transcription step performed in a single tube. However, a purification step cannot be performed unlike the case of using magnetic beads. For this reason, a residual reagent remains in a sample and inhibits PCR amplification. Then, assuming that the amount of a residual reagent contained in a cDNA sample prepared from a single-cell is defined as 100%, standard curves of samples containing 0%, 3%, 6% and 9% of a residual reagent were obtained (template: PCR product amplified by a standard template preparation PCR primer set of EEF1G gene (SEQ ID NOS: 4, 5); real-time PCR primer: sequence ID Nos. 12, 13; gene specific probe: Sequence No. 19). The inhibition effect of a residual reagent on PCR was studied. The results are shown in FIG. 8.

Figures 2, 8:
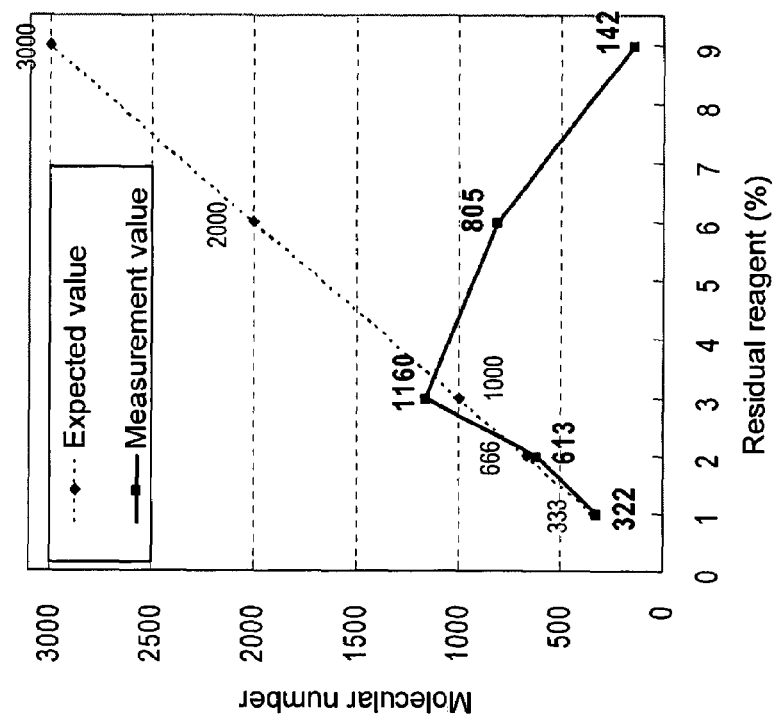
FIG. 8 shows the inhibition effects of a residual reagent on PCR based on standard curves in the cases where a residual reagent is 0%, 3%, 6% and 9% relative to the residual reagent contained in a cDNA sample prepared from a single-cell being 100%. The transverse axis of FIG. 8-1 indicates the molecular number of template and the vertical axis indicates a Ct (threshold cycle) value. The transverse axis of FIG. 8-2 indicates residual reagent (%) contained in an analysis sample and the vertical axis indicates the molecular number (measurement value)
Figures 1, 8:
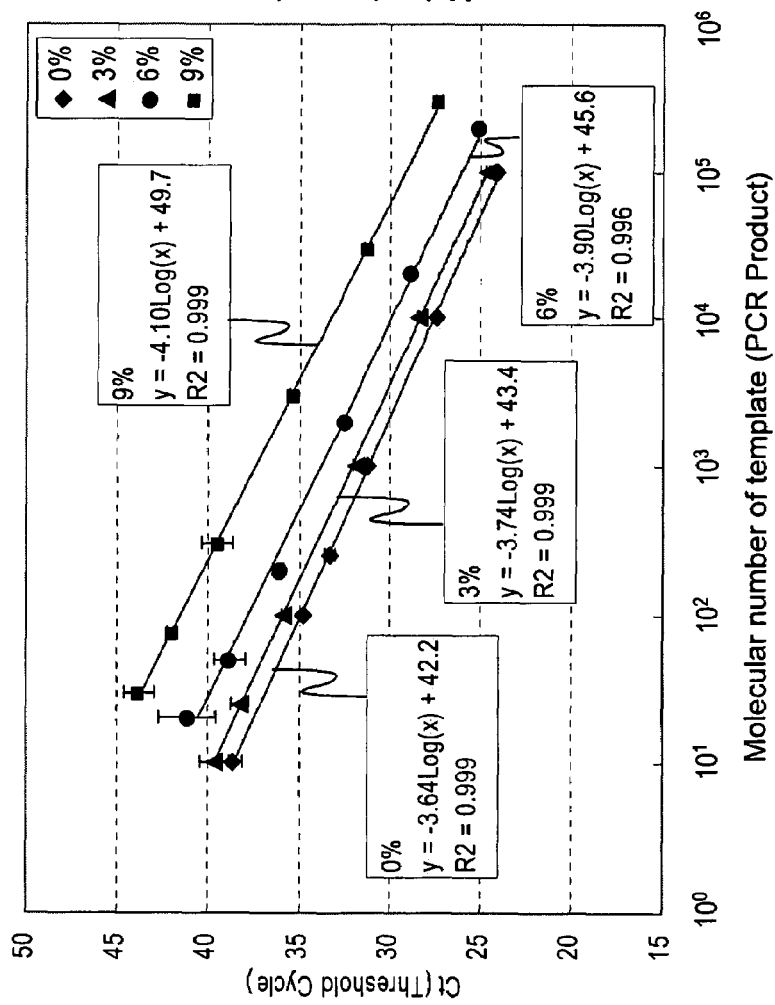

As is shown in FIG. 8-1, the inclination of the standard curve, which shows PCR amplification efficiency, greatly decreases as the amount of a residual reagent increases, as is apparent from comparison with the standard curve (0%) containing no residual reagent. Furthermore, samples containing a residual reagent in amounts of 1%, 2%, 3%, 6%, and 9% and templates (known concentration) in an amount of 333 molecules, 666 molecules, 1000 molecules, 2000 molecules and 3000 molecules, correspondingly, were analyzed by real-time PCR. The results are shown in FIG. 8-2. In the figure, a desired value is shown by a broken line. An actual value is shown in a solid line. These lines are consistent with each other until a residual reagent is 3%. However, when the residual reagent is more than 3%, the solid line greatly deviates from the broken line (desired value). Actually, it was difficult to determine the amount accurately. More specifically, in a conventional method for preparing cDNA from a single-cell in a single tube, the single-cell derived cDNA sample obtained is further divided into portions (at most 3%) and the divided portion must be used as a real-time PCR analysis sample. It may be a cause that a measurement sensitivity significantly decreases. In contrast, in the single-cell derived cDNA library fixed onto a carrier manufactured by the present invention, purification is successfully performed after reverse transcription. Therefore, the amount of a residual reagent in the sample is 0%. The whole amount of cDNA derived from a single-cell can be used as a real-time PCR analysis sample.

<Study on the Diameter and Number of Magnetic Beads in Reverse Transcription>

Figures 1, 9:
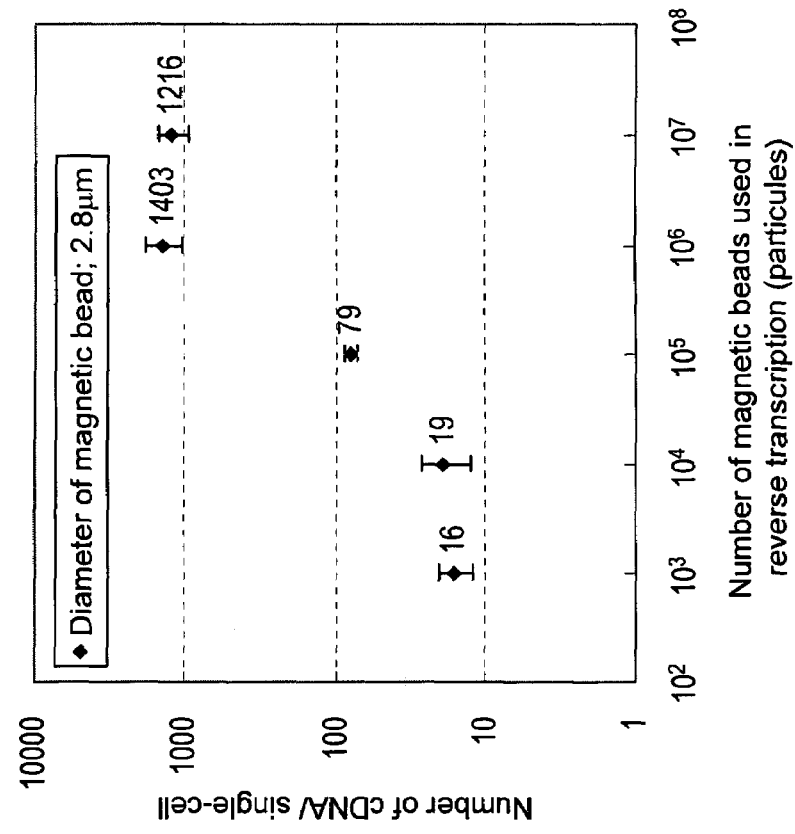
FIG. 9 shows the results with respect to the optimal number of magnetic beads in the step of performing reverse transcription of mRNA derived from a single-cell on the surface of a carrier in the method of the present invention.
Figures 2, 9:
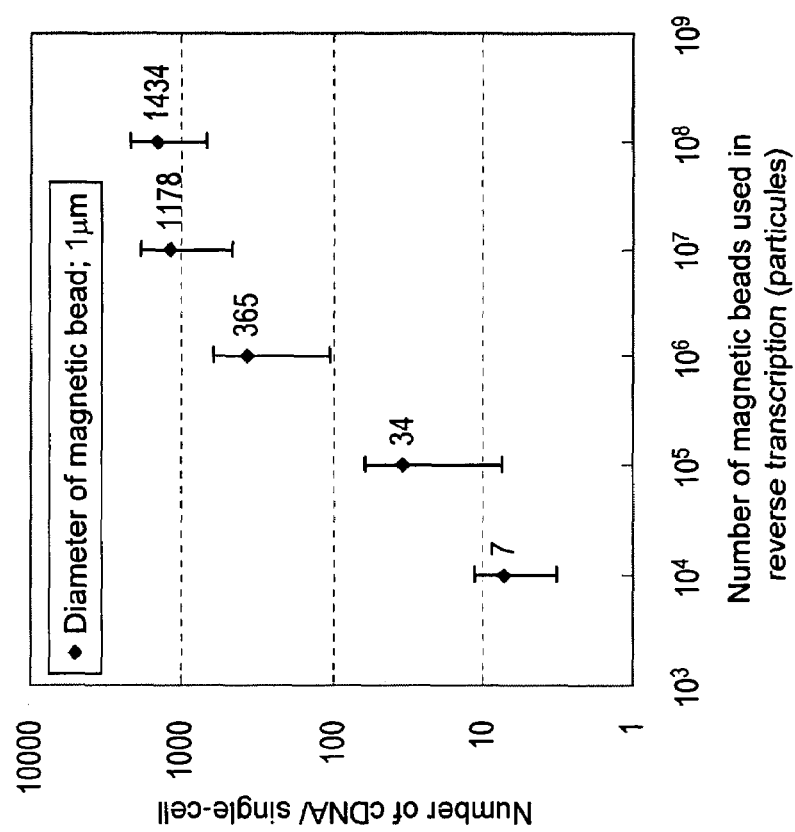
Figures 1, 10:
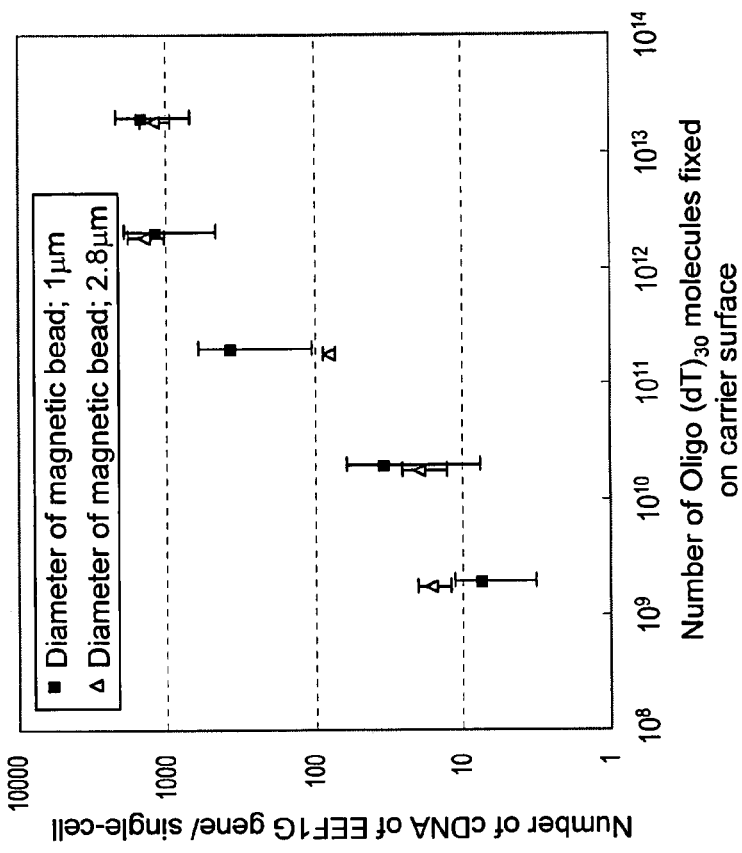
Figures 2, 10:
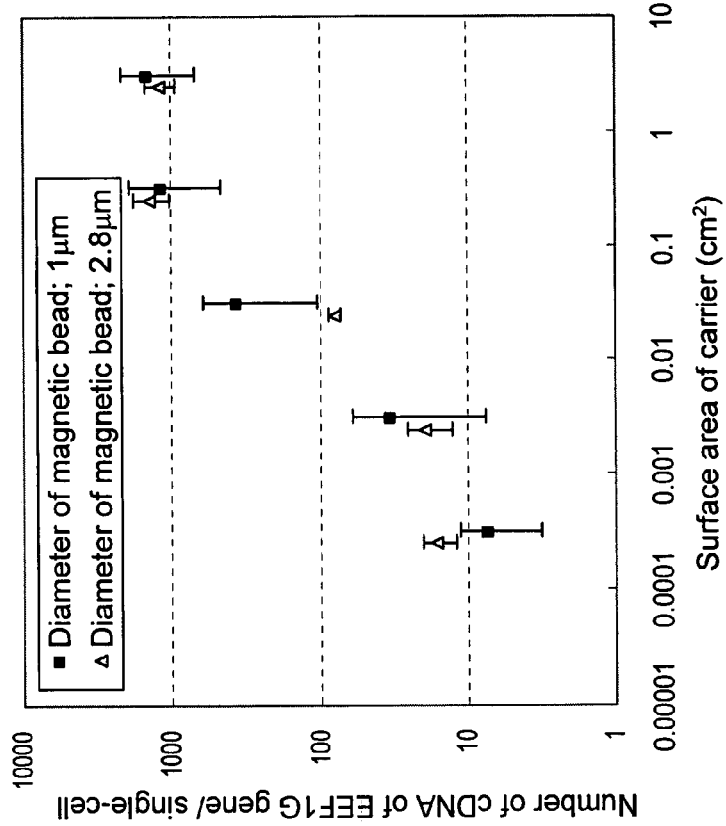

In the cases of magnetic beads having a diameter of 1 µm and 2.8 µm, the number of oligo (dT) molecules fixed onto a single magnetic bead is about $2\times10^5$ and $1.8\times10^6$, respectively. The amount of magnetic beads required for reverse transcription of mRNA molecules ($10^5$ to $10^6$ molecules) contained in a single cell may sufficient to be 5 (φ1 µm) or 1 (φ2.8 µm), if calculated based only on the number of oligo (dT) molecules. However, actually, it is presumed that the smaller the number of magnetic beads, the lower the reverse transcription efficiency. Conversely, when the number of magnetic beads is excessively large, detection of fluorescent emission is presumably inhibited in real time PCR. Then, to know an appropriate number of magnetic beads in the step of performing reverse transcription of a single-cell derived mRNA on the surface of magnetic beads (Step 1-4 of FIG. 1), EEF1G gene expressing about 1000 copies/cell was selected and investigation was made. As a result, when the number of magnetic beads of 1 µm in diameter was $10^7$ to $10^8$ and when the number of magnetic beads of 2.8 µm in diameter was $10^6$ to $10^8$, the measurement value of about 1000 copies were obtained, that is, the reaction efficiency is satisfactory (FIGS. 9-1 and 9-2). When a smaller number of magnetic beads were used, the measurement value (the number of copies) was significantly low. This is conceivably due to reverse transcription efficiency and carrier recovery efficiency. The results were further analyzed by plotting the total surface areas of the magnetic beads having a diameter of 1 µm and 2.8 µm on the transverse axis. As a result, it was found that reverse transcription efficiency does not change depending upon the diameter of magnetic beads. From the results, it was confirmed that when the total surface area of a carrier is about 0.1 $cm^2$ or more (the fixing amount of oligo (dT) on the surface of a carrier used in the example was about $5\times10^{13}$ molecules/$cm^2$), the reverse transcription is satisfactory (FIG. 10-1). When the plot on the transverse axis of this graph (FIG. 10-1) is changed to the total number of oligo (dT) molecule fixed onto the surface of a carrier, the graph shown in FIG. 10-2 is obtained. It was found that not less than $10^{12}$ of oligo (dT) molecules are required in step of performing reverse transcription of single-cell derived mRNA on the surface of magnetic beads.

Figures 1, 2, 11:
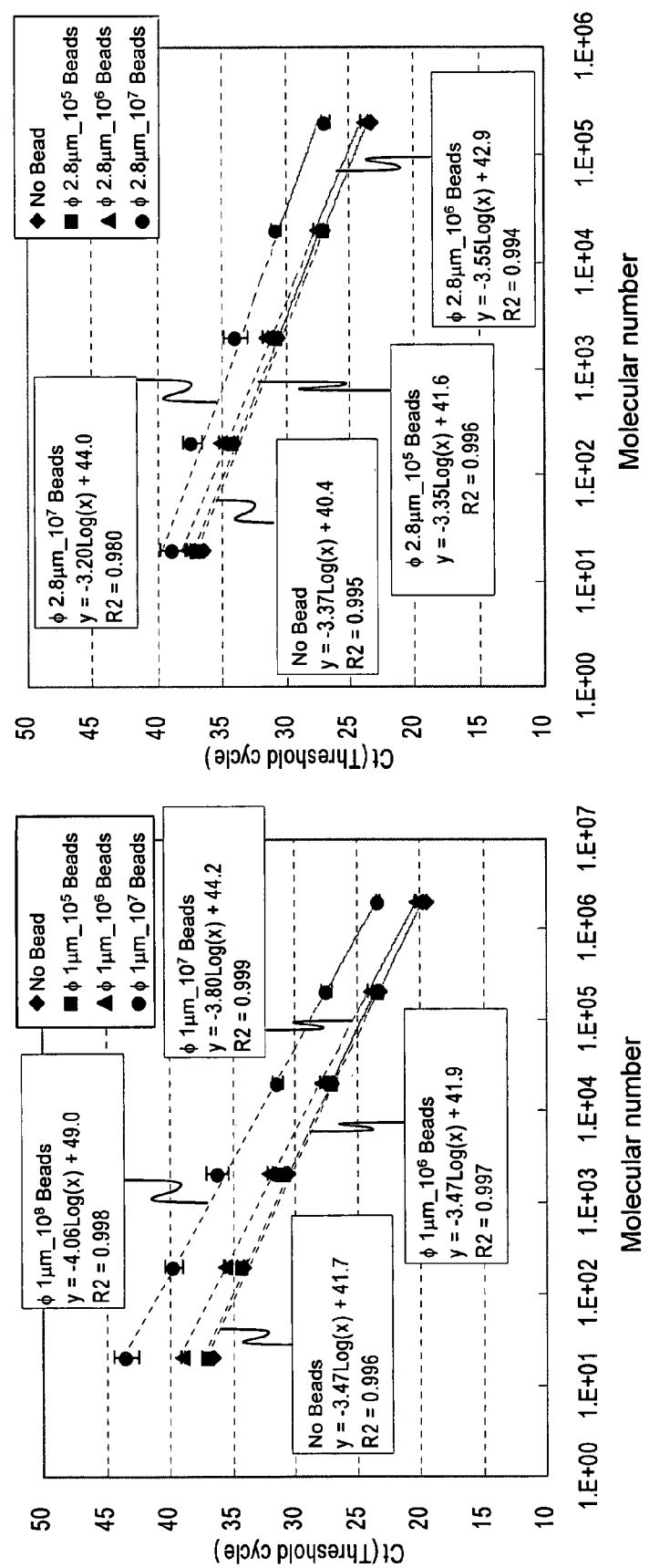
FIG. 11 shows the results with respect to the optimal number of magnetic beads in the step of detecting amplification amount in the method of the present invention.
Figure 12:
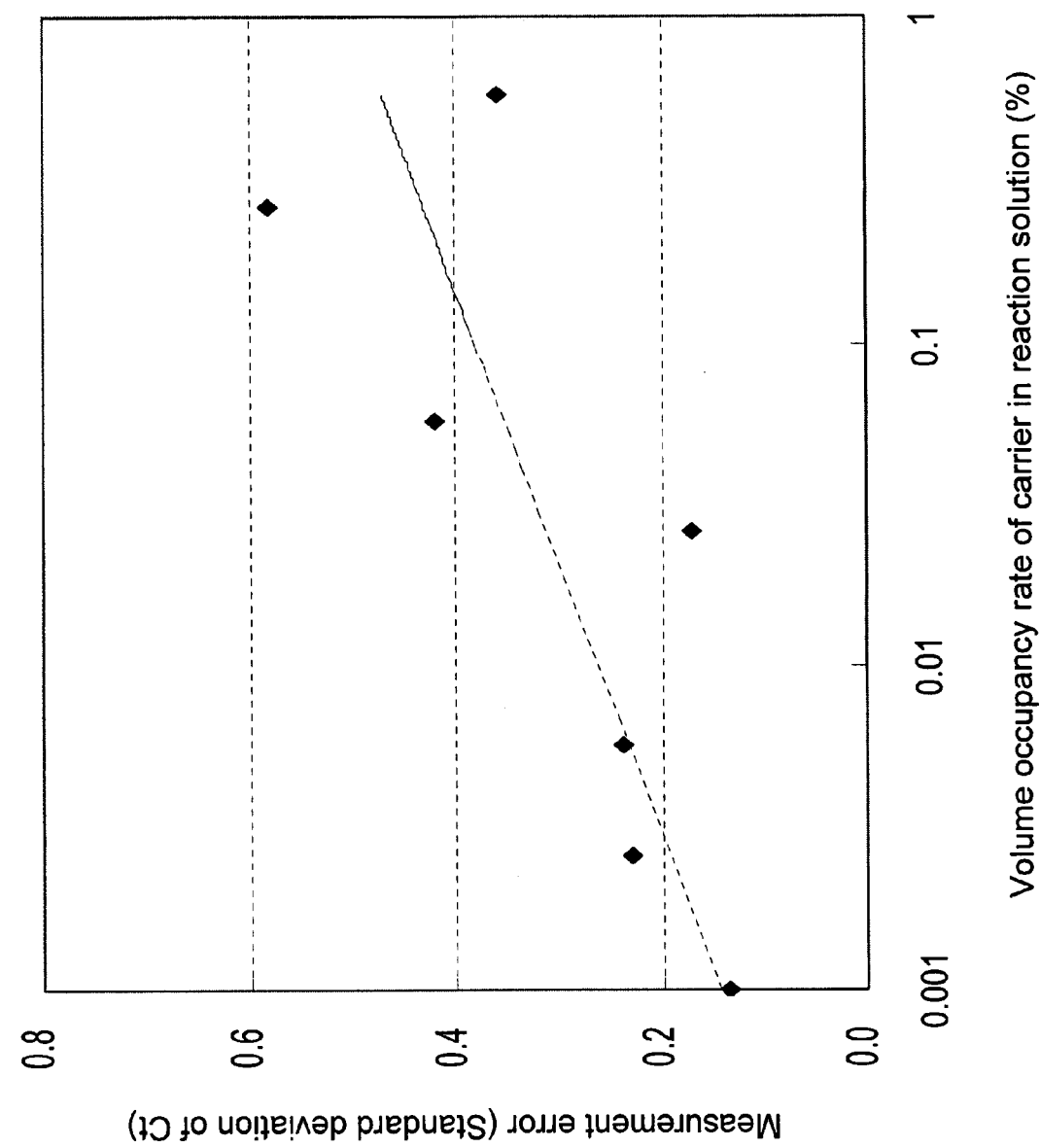
FIG. 12 shows the results with respect to an optimal volume occupancy rate of carrier in a reaction solution in the step of detecting amplification amount in the method of the present invention. The transverse axis indicates a volume occupancy rate of carrier in a reaction solution and the vertical axis indicates measurement error (standard deviation of Ct value).

On the other hand, in a step of detecting an amplification amount, the optimal number of magnetic beads was investigated. A PCR product, which was amplified by use of a standard template preparation PCR primer set of EEF1G gene (SEQ ID NOS: 4 and 5) and fixed onto magnetic beads, was used as a template, a real-time PCR primer set (SEQ ID NOS: 12 and 13) and a gene specific probe (SEQ ID NO: 19) were used. The results of the Example obtained by use of magnetic beads having a diameter of 1 µm and 2.8 µm are shown in FIGS. 11-1 and 11-2, respectively. Both figures show that with an increase of the number of magnetic beads, a standard curve shifts upward, meaning that signal detection is inhibited. The degree of inhibition is constant depending upon the number of magnetic beads. Therefore, $R^2$ value is still high. It was confirmed that quantification measurement can be performed as long as magnetic beads of 1 µm in diameter are present up to $10^8$ and magnetic beads of 2.8 µm in diameter are present up to about $10^7$. However, as shown by an error bar in the graph, a measurement error increases with an increase of the number of magnetic beads. If analysis is made using magnetic beads more than the aforementioned number, measurement accuracy may possibly decrease significantly. More specifically, referring to the graph (FIG. 12) whose transverse axis expresses a volume occupancy rate of carrier in a reaction solution and whose vertical axis expresses a measurement error (standard deviation ($\sigma$) of a Ct value), it is confirmed that as the volume occupancy rate of carrier increases, the measurement error increases, decreasing measurement accuracy. Consequently, an appropriate volume occupancy rate of carrier in a reaction solution is not more than 1%, and further preferably 0.1% or less when a quantification measurement is more accurately performed.

<Studies on the Number of Cells to be Used as an Analysis Sample>

Figure 7:
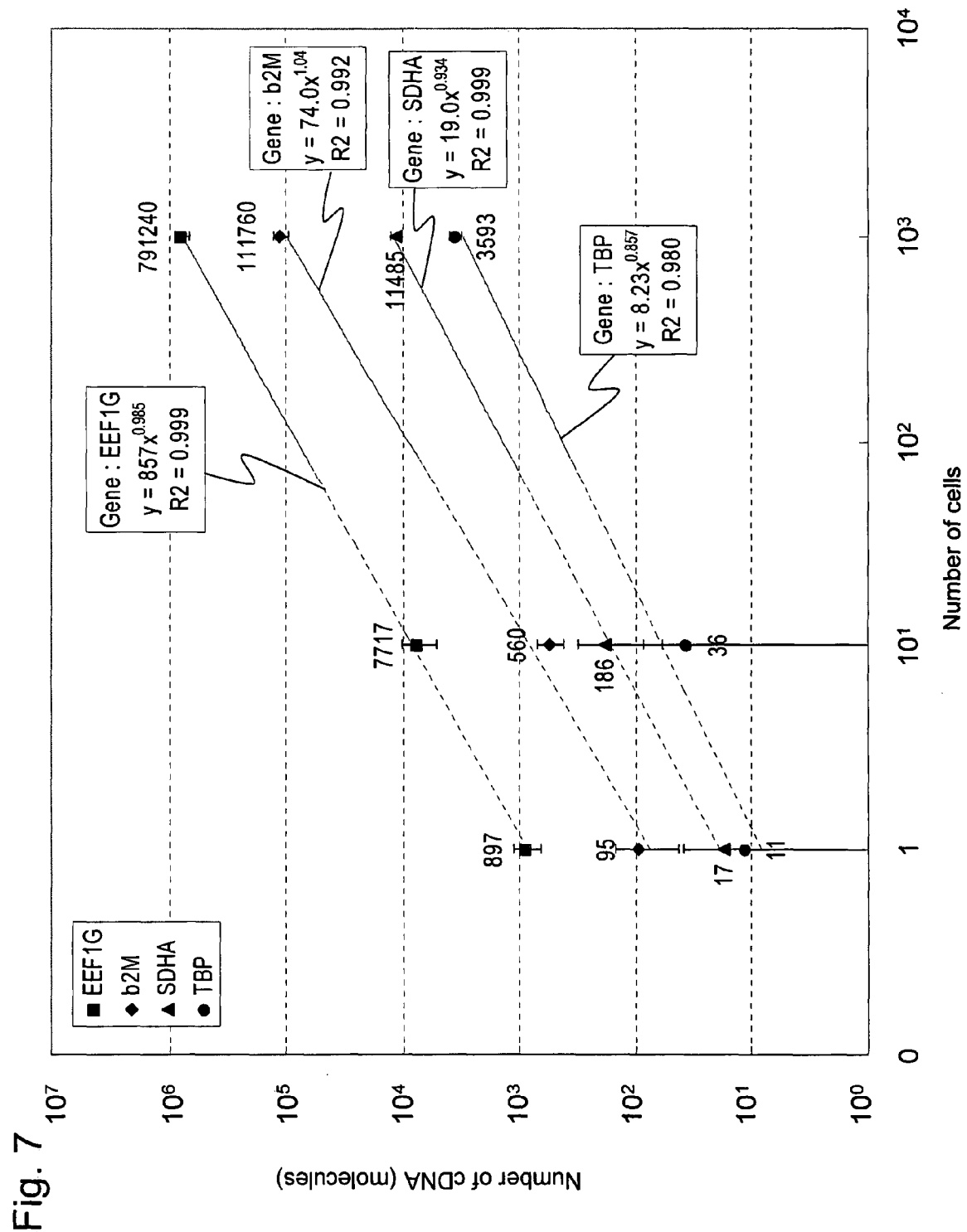
FIG. 7 shows the results of determining the number of cDNA molecules (corresponding to the number of copies of mRNA molecules) contained in a sample by the method of the present invention with respect to single-cell samples (n=6), ten-cell samples (n=3) and thousand-cell samples (n=3). The transverse axis indicates the number of cells and the vertical axis indicates the number of copies.

When cells as small as $10^3$ or less are used as an analysis sample, conventional methods have a problem of low sensitivity and large measurement error. In contrast, highly accurate quantitative analysis can be made by the method of the present invention, even if a plurality of cells (up to $10^3$ cells) is used, as shown in FIG. 7.

All publications, patents, and patent applications cited herein are incorporated herein by reference in their entirety.

What is claimed is:

1. A method of detecting a nucleic acid, said method comprising in sequence:

picking up a whole single-cell from a sample containing at least a single-cell having a cell membrane, lysing the cell membrane of the sampled whole single-cell and extracting nucleic acids from the cell, degrading DNA of the extracted nucleic acids with DNase, hybridizing mRNA of the total RNA contained in the whole single-cell with oligo (dT) fixed onto a carrier, said carrier consisting of particles and the total surface area of the particles is from 0.1 $cm^2$ to and including 10 $cm^2$, a volume occupancy rate of the particles in an amplification reaction solution is 1% or less, and a total number of oligo (dT) molecules fixed onto the carrier is $10^{12}$ or more, performing reverse transcription of the mRNA hybridized with the oligo (dT) to fix cDNA derived from the single-cell onto the carrier, thereby preparing a single-cell derived cDNA library fixed onto a carrier, and amplifying cDNA fixed onto the carrier and simultaneously detecting an amplification amount of the cDNA.

2. The method of detecting a nucleic acid according to claim 1, wherein during the DNase treatment, hybridizing mRNA of the total RNA contained in the single-cell with oligo (dT) fixed onto a carrier, and performing reverse transcription of the mRNA hybridized with oligo (dT) to fix cDNA derived from the single-cell onto the carrier, thereby preparing a single-cell derived cDNA library fixed onto a carrier, are performed in a single tube.

3. The method of detecting a nucleic acid according to claim 1, further comprising, after amplifying cDNA fixed onto the carrier and simultaneously detecting an amplification amount of the cDNA, (a) recovering and washing the carrier and (b) amplifying the cDNA fixed onto the carrier and simultaneously detecting the amplified amount.

4. The method of detecting a nucleic acid according to claim further comprising, after (b), repeating (a) and (b).

5. The method of detecting a nucleic acid according to claim 1, wherein, when preparing a single-cell derived cDNA library fixed onto a carrier, substantially all mRNA molecules contained in the single-cell are hybridized.

6. The method of detecting a nucleic acid according to claim 1, wherein a volume occupancy rate of the particles in the amplification reaction solution is 0.1% or less.

7. The method of detecting a nucleic acid according to claim 1, wherein the diameter of the particles is 1 μm and the number of the particles is $10^7$ to $10^8$.

8. The method of detecting a nucleic acid according to claim 1, wherein the diameter of the particles is 2.8 μm and the number of the particles is $10^6$ to $10^7$.

9. The method of detecting a nucleic acid according to claim 1, wherein the carrier consists of magnetic beads.

* * * * *

UNITED STATES PATENT AND TRADEMARK OFFICE
CERTIFICATE OF CORRECTION

| | |
|---|---|
| PATENT NO. | : 8,802,367 B2 |
| APPLICATION NO. | : 11/783575 |
| DATED | : August 12, 2014 |
| INVENTOR(S) | : Taniguchi et al. |

Page 1 of 1

It is certified that error appears in the above-identified patent and that said Letters Patent is hereby corrected as shown below:

IN THE CLAIMS:

Column 25, line 63 change "area of the particles is from 0.1 $cm^2$ to and including 10"
to -- area of the particles is from 0.1 $cm^2$ up to and including 10 --.

Column 27, line 6 change "claim further comprising, after (b), repeating (a) and (b)"
to -- claim 3 further comprising, after (b), repeating (a) and (b) --.

Signed and Sealed this
Seventh Day of April, 2015

Michelle K. Lee
*Director of the United States Patent and Trademark Office*